US009957526B2

(12) United States Patent
Holmes et al.

(10) Patent No.: US 9,957,526 B2
(45) Date of Patent: May 1, 2018

(54) DELIVERY METHODS AND COMPOSITIONS FOR NUCLEASE-MEDIATED GENOME ENGINEERING

(71) Applicant: Sangamo BioSciences, Inc., Richmond, CA (US)

(72) Inventors: Michael C. Holmes, Richmond, CA (US); Jianbin Wang, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 0 days. days.

(21) Appl. No.: 14/516,236

(22) Filed: Oct. 16, 2014

(65) Prior Publication Data

US 2015/0110762 A1    Apr. 23, 2015

Related U.S. Application Data

(60) Provisional application No. 61/892,348, filed on Oct. 17, 2013, provisional application No. 62/033,424, filed on Aug. 5, 2014.

(51) Int. Cl.
*C12N 15/85*     (2006.01)
*C12N 15/90*     (2006.01)

(52) U.S. Cl.
CPC .. *C12N 15/907* (2013.01); *C12N 2750/14143* (2013.01)

(58) Field of Classification Search
CPC .................... C12N 15/907; C12N 2750/14143
See application file for complete search history.

(56) References Cited

U.S. PATENT DOCUMENTS

| | | | |
|---|---|---|---|
| 5,789,538 | A | 8/1998 | Rebar et al. |
| 5,925,523 | A | 7/1999 | Dove et al. |
| 6,007,988 | A | 12/1999 | Choo |
| 6,013,453 | A | 1/2000 | Choo |
| 6,140,081 | A | 10/2000 | Barbas |
| 6,140,466 | A | 10/2000 | Barbas, III et al. |
| 6,140,815 | A | 10/2000 | Green et al. |
| 6,200,759 | B1 | 3/2001 | Dove et al. |
| 6,242,568 | B1 | 6/2001 | Barbas, III et al. |
| 6,410,248 | B1 | 6/2002 | Greisman et al. |
| 6,453,242 | B1 | 9/2002 | Eisenberg et al. |
| 6,479,626 | B1 | 11/2002 | Kim et al. |
| 6,503,717 | B2 | 1/2003 | Case et al. |
| 6,534,261 | B1 | 3/2003 | Cox, III et al. |
| 6,599,692 | B1 | 7/2003 | Case et al. |
| 6,607,882 | B1 | 8/2003 | Cox, III et al. |
| 6,689,558 | B2 | 2/2004 | Case |
| 6,723,551 | B2 | 4/2004 | Kotin et al. |
| 6,794,136 | B1 | 9/2004 | Eisenberg et al. |
| 6,824,978 | B1 | 11/2004 | Cox, III et al. |
| 6,903,185 | B2 | 6/2005 | Kim et al. |
| 6,933,113 | B2 | 8/2005 | Case et al. |
| 6,979,539 | B2 | 12/2005 | Cox, III et al. |
| 7,013,219 | B2 | 3/2006 | Case et al. |
| 7,067,317 | B2 | 6/2006 | Rebar et al. |
| 7,070,934 | B2 | 7/2006 | Cox, III et al. |
| 7,153,949 | B2 | 12/2006 | Kim et al. |
| 7,163,824 | B2 | 1/2007 | Cox, III et al. |
| 7,253,273 | B2 | 8/2007 | Collingwood |
| 7,262,054 | B2 | 8/2007 | Jamieson et al. |
| 7,361,635 | B2 | 4/2008 | Miller et al. |
| 7,888,121 | B2 | 2/2011 | Urnov et al. |
| 7,914,796 | B2 | 3/2011 | Miller et al. |
| 7,951,925 | B2 | 5/2011 | Ando et al. |
| 7,972,854 | B2 | 7/2011 | Miller et al. |
| 8,034,598 | B2 | 10/2011 | Miller |
| 8,110,379 | B2 | 2/2012 | DeKelver et al. |
| 8,329,986 | B2 | 12/2012 | Butler et al. |
| 8,399,218 | B2 | 3/2013 | Gupta et al. |
| 8,409,861 | B2 | 4/2013 | Guschin et al. |
| 8,563,314 | B2 | 10/2013 | Gregory et al. |
| 8,586,526 | B2 | 11/2013 | Gregory et al. |
| 8,623,618 | B2 | 1/2014 | Doyon et al. |
| 8,697,359 | B1 | 4/2014 | Zhang |
| 8,772,453 | B2 | 7/2014 | Paschon et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2006/0063231 | A1 | 3/2006 | Li et al. |
| 2006/0188987 | A1 | 8/2006 | Guschin et al. |
| 2007/0218528 | A1 | 9/2007 | Miller |
| 2008/0131962 | A1 | 6/2008 | Miller |

(Continued)

FOREIGN PATENT DOCUMENTS

GB          2338237 A      12/1999
WO      WO 95/19431 A1     7/1995

(Continued)

OTHER PUBLICATIONS

Aiuti, et al., "Lentiviral Hematopoietic Stem Cell Gene Therapy in Patients With Wiskott-Aldrich Syndrome," *Science* 23(341):6148 (2013) doi: 10.1126/science.1233151.
Beerli, et al., "Engineering Polydactyl Zinc-Finger Transcription Factors," *Nature Biotechnol.* 20:135-141(2002).
Boch, et al., "Breaking the Code of DNA Binding Specificity of Tal-Type III Effectors," *Science* 326:1509-1512 (2009).
Bonas, et al., "Genetic and Structural Characterization of the Avirulence Gene AVRBS3 From Xanthomonas Campestris PV. Vesicatoria," *Mol. Gen. Genet.* 218:127-136 (1989).
Chang, et al., "Modification of DNA Ends Can Decrease End Joining Relative to Homologous Recombination in Mammalian Cells," *Proc. Natl. Acad. Sci. USA* 84:4959-4963 (1987).
Choo, et al., "Advances in Zinc Finger Engineering," *Curr. Opin. Struct. Biol.* 10:411-416 (2000).
Cong, et al., "Multiplex Genome Engineering Using CRISPR/CAS Systems," *Sciencexpress* 1/10.1126/science 1231143 (2013).
Genovese, et al., "Targeted Genome Editing in Human Repopulating Haematopoietic Stem Cells," *Nature* 510:235-240 (2014).
Grimm and Kay, "From Virus Evolution to Vector Revolution: Use of Naturally Occurring Serotypes of Adeno-Associated Virus (AAV) as Novel Vectors for Human Gene Therapy," *Current Gene Therapy* 3:281-304 (2003).

(Continued)

*Primary Examiner* — Thaian N Ton
(74) *Attorney, Agent, or Firm* — Pasternak Patent Law; Susan Abrahamson

(57) ABSTRACT

The present disclosure is in the field of genome engineering, particularly targeted modification of the genome of a cell.

7 Claims, 10 Drawing Sheets

(56) References Cited

U.S. PATENT DOCUMENTS

| | | |
|---|---|---|
| 2008/0159996 A1 | 7/2008 | Ando et al. |
| 2008/0299580 A1 | 12/2008 | DeKelver et al. |
| 2009/0068164 A1 | 4/2009 | Segal et al. |
| 2010/0047805 A1 | 2/2010 | Wang |
| 2010/0065123 A1 | 3/2010 | Gust et al. |
| 2010/0199389 A1 | 8/2010 | Butler et al. |
| 2010/0218264 A1 | 8/2010 | Cui et al. |
| 2011/0201055 A1 | 8/2011 | Doyon et al. |
| 2011/0207221 A1 | 8/2011 | Cost et al. |
| 2011/0265198 A1 | 10/2011 | Gregory et al. |
| 2012/0017290 A1 | 1/2012 | Cui et al. |
| 2012/0128635 A1* | 5/2012 | Gregory ............. A61K 31/7088 424/93.6 |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2013/0326645 A1 | 12/2013 | Cost et al. |
| 2015/0056705 A1 | 2/2015 | Conway et al. |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 07/014275 A2 | 2/2007 |
| WO | WO 07/030674 A2 | 3/2007 |
| WO | WO 10/079430 A1 | 7/2010 |
| WO | WO 11/078665 A1 | 6/2011 |
| WO | WO 2013/063315 A2 | 5/2013 |
| WO | WO 2015/127439 A1 | 8/2015 |
| WO | WO 2012/021632 A2 | 2/2016 |

OTHER PUBLICATIONS

Grossman, et al., "Successful Ex Vivo Gene Therapy Directed to Liver in a Patient With Familial Hypercholesterolaemia," *Nature Genetics* 6:335-341 (1994) doi:10.1038/ng0494-335.

Guo, et al., "Directed Evolution of an Enhanced and Highly Efficient FokI Cleavage Domain for Zinc Finger Nucleases," *J. Mol. Biol.* 400(1):96-107 (2010).

Haft, et al., "A Guild of 45 CRISPR-Associated (CAS) Protein Families and Multiple CRISPR/CAS Subtypes Exist in Prokaryotic Genomes," *PLoS Comput. Biol.* 1(6):474-483 (2005).

Heuer, et al., "Repeat Domain Diversity of AVRBS3-Like Genes in Ralstonia Solanacearum Strains and Association With Host Preferences in the Field," *Appl. and Envir. Micro.* 73(13):4379-4384 (2007).

Isalan, et al., "A Rapid, Generally Applicable Method to Engineer Zinc Fingers Illustrated by Targeting the HIV-1 Promoter," *Nat. Biotechnol.* 19:656-660 (2001).

Jansen, et al., "Identification of Genes That Are Associated With DNA Repeats in Prokaryotes," *Molecular Microbiology* 43(6):1565-1575 (2002).

Kay, et al., "A Bacterial Effector Acts as a Plant Transcription Factor and Induces a Cell Size Regulator," *Science* 318:648-651 (2007).

Kim, et al., "Hybrid Restriction Enzymes:Zinc Finger Fusions to FOK 1 Cleavage Domain," *Proc. Natl. Acad. Sci. USA* 93(3):1156-1160 (1996).

Makarova, et al., "A DNA Repair System Specific for Thermophilic Archaea and Bacteria Predicted by Genomic Context Analysis," *Nucleic Acids Res.* 30:482-496 (2002).

Makarova, et al., "A Putative RNA-Interference-Based Immune System in Prokaryotes: Computational Analysis of the Predicted Enzymatic Machinery, Functional Analogies With Eukaryotic RNAi, and Hypothetical Mechanisms of Action," *Biol. Direct* 1:7 (2006).

Miller, et al., "An Improved Zinc-Finger Nuclease Architecture for Highly Specific Genome Editing," *Nat. Biotechnol.* 25:778-785 (2007).

Moscou, et al., "A Simple Cipher Governs DNA Recognition by Tal Effectors," *Science* 326:1501 (2009).

Nehls, et al., "Two Genetically Separable Steps in the Differentiation of Thymic Epithelium," *Science* 272(5263):886-889 (1996).

Olovnikov, et al., "Bacterial Argonaute Samples the Transcriptome to Identify Foreign DNA," *Mol. Cell.* 51(5):594-605 (2013).

Pabo, et al., "Design and Selection of Novel CYS2HIS2 Zinc Finger Proteins," *Ann. Rev. Biochem.* 70:313-340 (2001).

Schornack, et al., "Gene-For-Gene-Mediated Recognition of Nuclear-Targeted AVRBS3-Like Bacterial Effector Proteins," *J. Plant Physiol.* 163(3):256-272 (2006).

Segal, et al., "Custom DNA-Binding Proteins Come of Age: Polydactyl Zinc-Finger Proteins," *Curr. Opin. Biotechnol.* 12:632-637 (2001).

Sheng, et al., "Structure-Based Cleavage Mechanism of Thermus Thermophilus Argonaute DNA Guide Strand-Mediated DNA Target Cleavage," *Proc. Natl. Acad. Sci. USA* 111(2):652-657 (2013) doi: 10.1073/pnas.1321032111.

Stella, et al., "CD34-Positive Cells: Biology and Clinical Relevance," *Haematologica* 80:367-387 (1995).

Swarts, et al., "DNA-Guided DNA Interference by a Prokaryotic Argonaute," *Nature* 507(7491):258-261 (2014).

Tebas, et al., "Gene Editing of CCR5 in Autologous CD4 T Cells of Persons Infected With HIV," *New England J. Med.* 370(10):901 (2014).

Vogel, "Biochemistry. A Bacterial Seek-and-Destroy System for Foreign DNA," *Science* 344(6187):972-973 (2014) doi: 10.1126/science.1252962.

Yuan, et al., "Crystal Structure of A. Aeolicus Argonaute, A Site-Specific DNA-Guided Endoribonuclease, Provides Insights Into Risc-Mediated MRNA Cleavage," *Molecular Cell* 19:405-419 (2005) doi: 10.1016/j.molcel.2005.07.011.

Benabdallah et al., "Targeted Gene Addition to Human Mesenchymal Stromal Cells as a Cell-Based Plasma-Soluble Protein Delivery Platform," Cytotherapy, vol. 12, No. 3, pp. 394-399 (2010).

Kandavelou et al., "Targed Manipulation of Mammalian Genomes Using Designed Zinc Finger Nucleases," Biochemical and Biophysical Research Communications, vol. 388, No. 1, pp. 56-61 (2009).

Lombardo et al., "Gene Editing in Human Stem Cells Using Zinc Finger Nucleases and Integrase-Defective Lentiviral Vector Delivery," Nature Biotechnology, vol. 25, No. 11, pp. 1298-1306 (2007).

Ramalingam et al., "Generation and Genetic Engineering of Human Induced Pluripotent Stem Cells Using Designed Zinc Finger Nucleases," Stem Cells and Development, vol. 22, No. 4, pp. 595-610 (2012).

van Renburg et al., "Chromatin Structure of Two Genomic Sites for Targeted Transgene Integration in Induced Pluripotent Stem Cells and Hematopoietic Stem Cells," Gene Therapy, vol. 20, No. 2, pp. 201-214 (2012).

* cited by examiner

Figure 2A
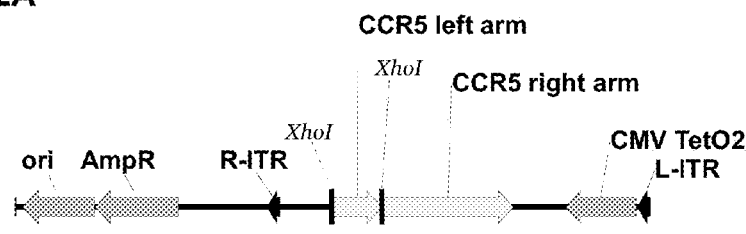
R5-160-XhoI donor
6562 bp
Figure 2B
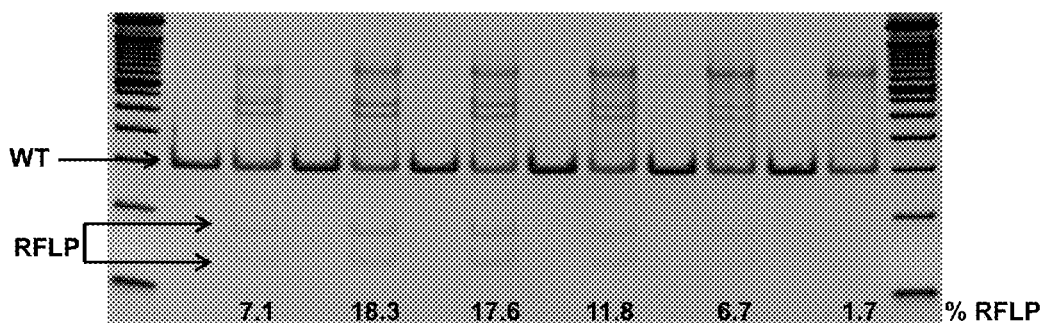
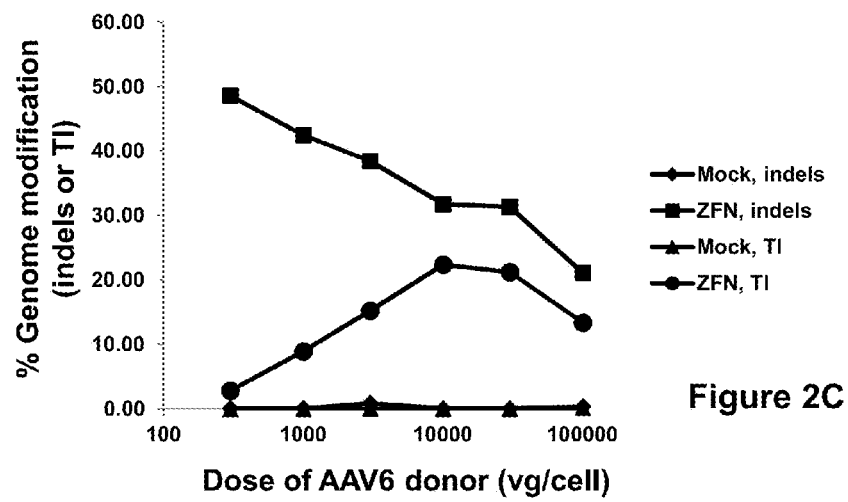
Figure 2C

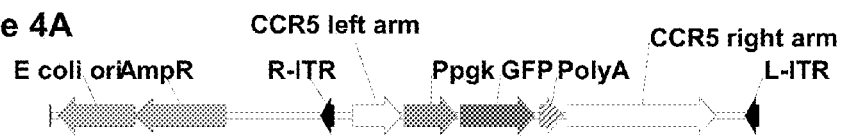
Figure 4A
R5-pgk-GFP-pA donor
6817 bp
Figure 4B
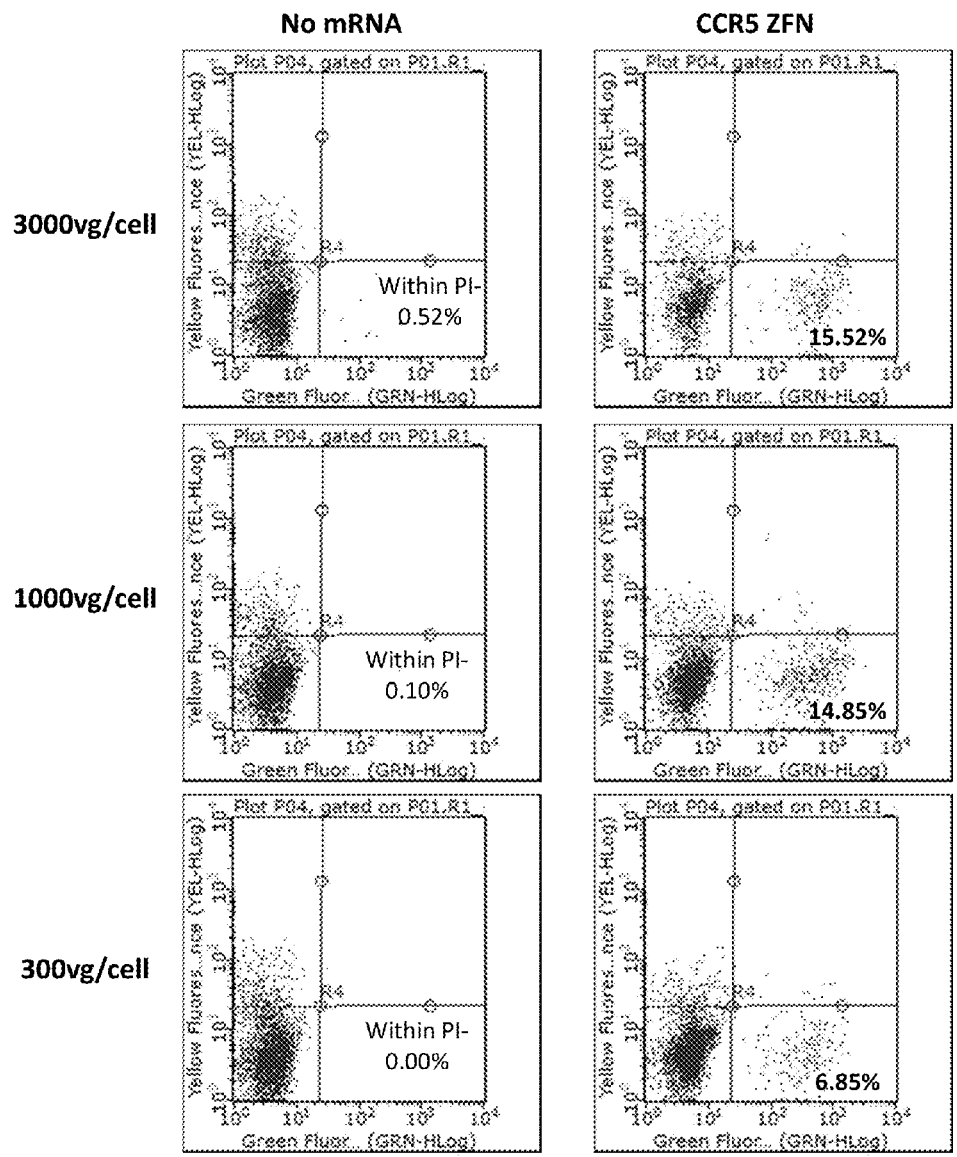

Figure 4C
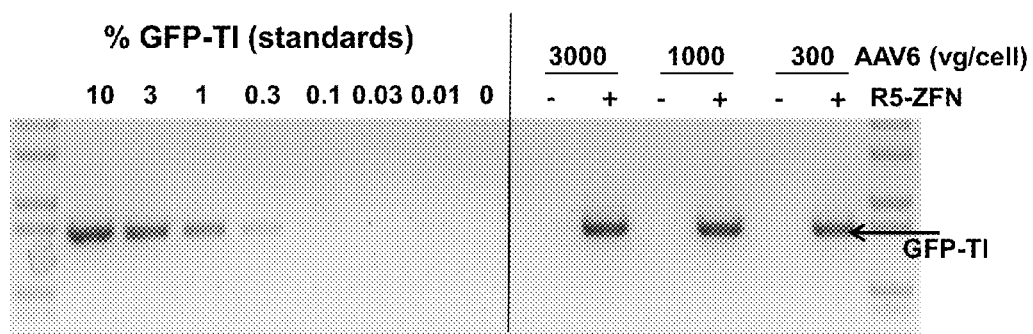
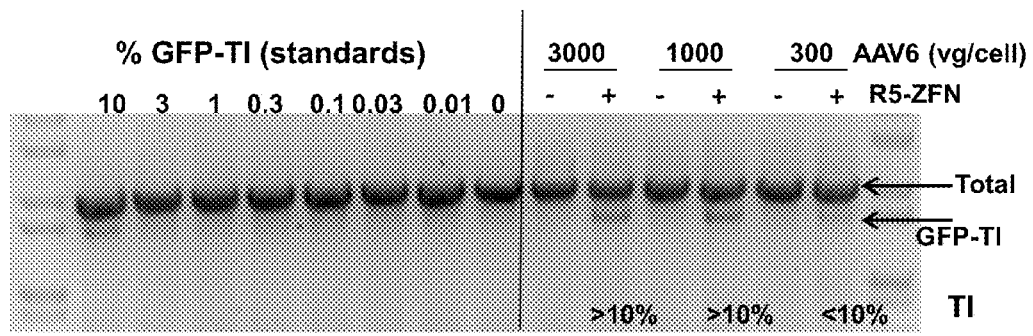
Figure 4D

AAVS1-HindIII donor
6387 bp

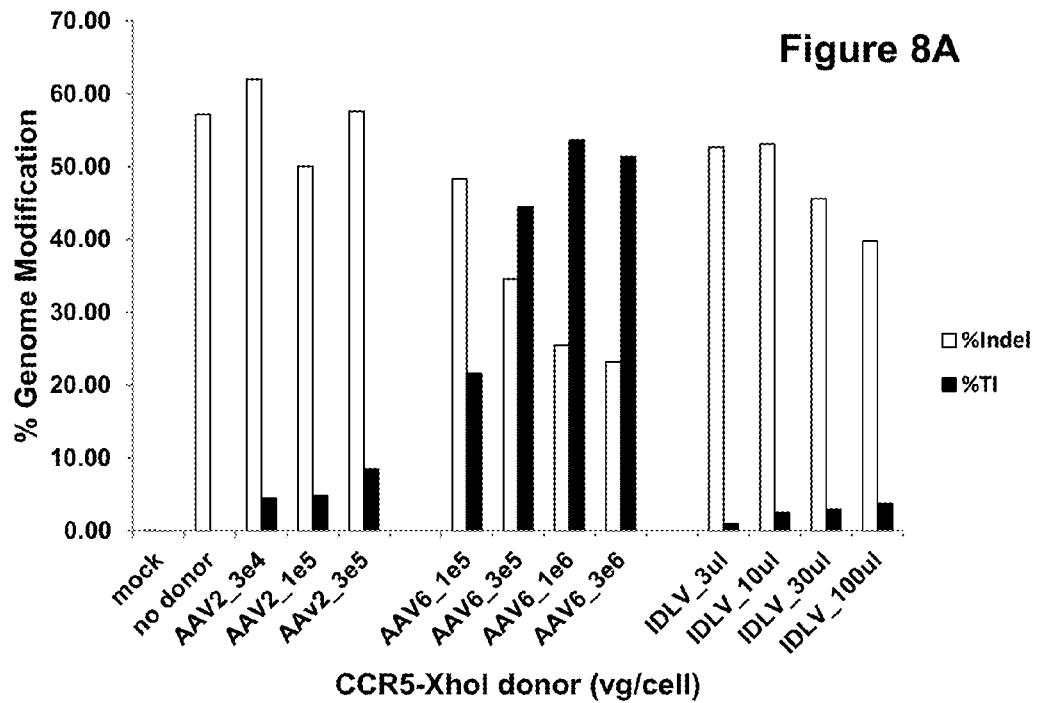
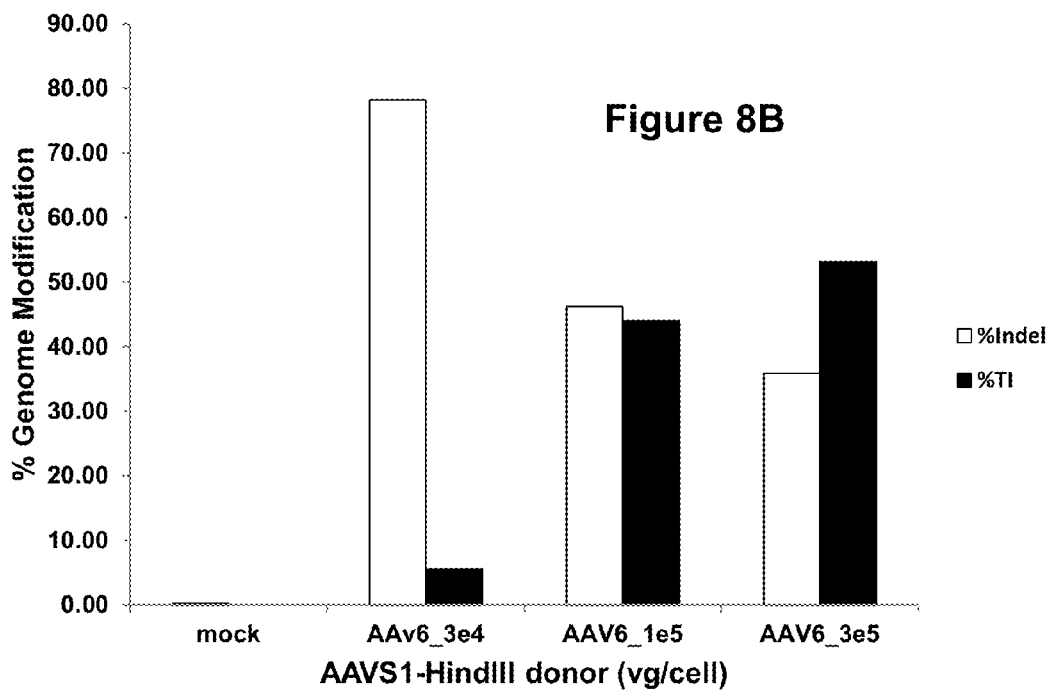

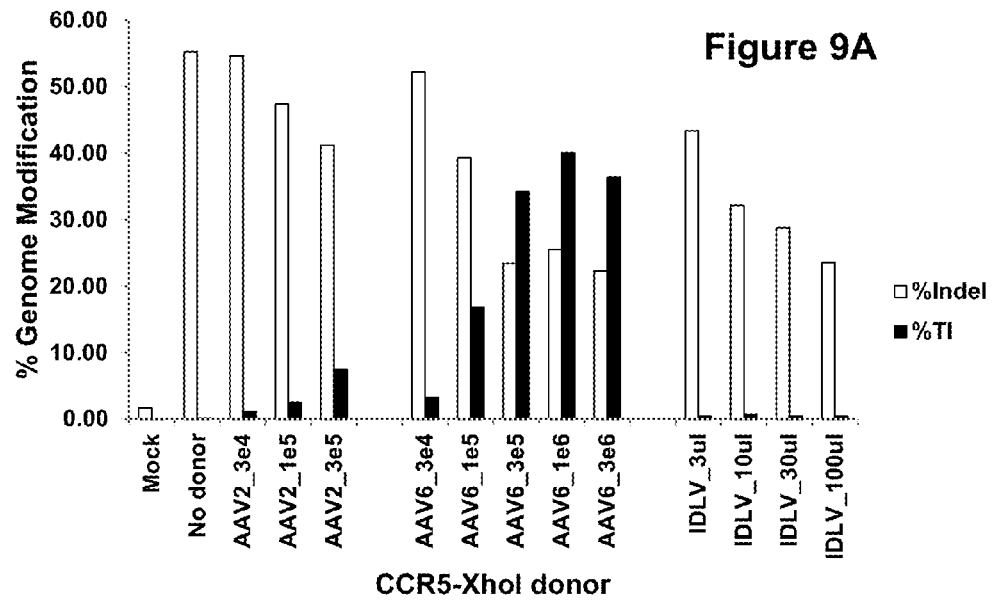
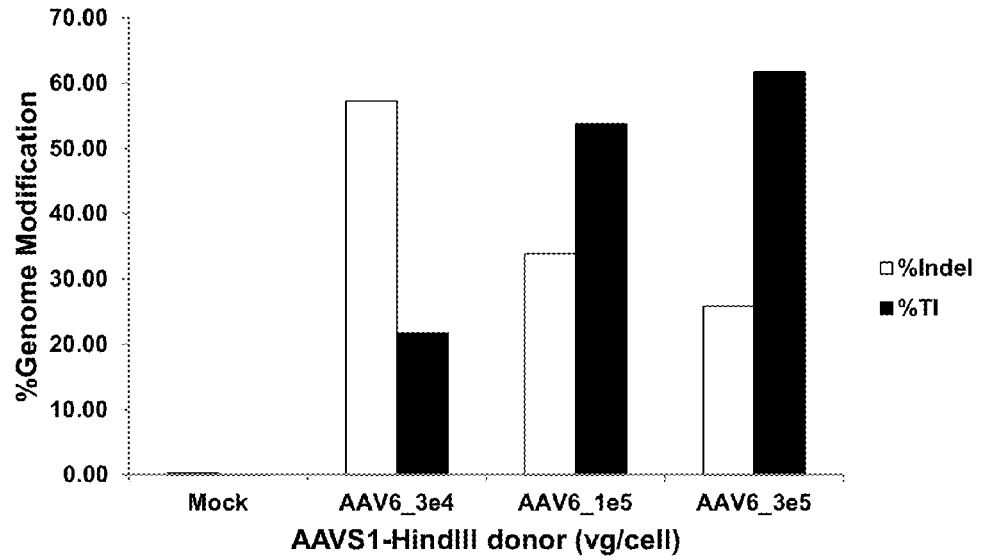
Figure 9B

SEQUENCE LISTING

```
<160> NUMBER OF SEQ ID NOS: 31

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctgtgcttca aggtccttgt ctgc                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctctgtctcc ttctacagcc aagc                                          24

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aagatggatt atcaagtgtc aagtcc                                        26

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caaagtccca ctgggcg                                                  17

<210> SEQ ID NO 5
<211> LENGTH: 59
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<221> NAME/KEY: modified_base
<222> LOCATION: (34)..(38)
<223> OTHER INFORMATION: a, c, t, g, unknown or other

<400> SEQUENCE: 5
acactctttc cctacacgac gctcttccga tctnnnnngc caggttgagc aggtagatg      59

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agacgtgtgc tcttccgatc tgctctactc actggtgttc atcttt                    46

<210> SEQ ID NO 7
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)..(37)
<223> OTHER INFORMATION: a, c, t, g, unknown or other

<400> SEQUENCE: 7
aatgatacgg cgaccaccga gatctacacn nnnnnnnaca ctctttccct acacgacgct     60
ctt                                                                   63

<210> SEQ ID NO 8
<211> LENGTH: 66
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(32)
<223> OTHER INFORMATION: a, c, t, g, unknown or other

<400> SEQUENCE: 8
caagcagaag acggcatacg agatnnnnnn nngtgactgg agttcagacg tgtgctcttc     60
cgatct                                                                66

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaggattggg aagacaatag cag                                             23

<210> SEQ ID NO 10
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccagcaatag atgatccaac tcaaattcc                                   29

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatttgcaca gctcatctgg c                                           21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccatcttgtt ccaccctgtg c                                           21

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Asp His Leu Ser Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Ser Gly His Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Asn Trp His Leu Gln Arg
1               5
```

```
<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Asp His Leu Thr Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His Asn Tyr Ala Arg Asp Cys
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Asn Ser Thr Arg Ile Gly
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Arg Ser Asn Leu Ser Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Lys Gln His Leu Thr Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21
```

Thr Ser Gly Asn Leu Thr Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Arg Asp Trp Arg Arg Asp
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Ser Ser His Leu Thr Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Leu Asp Asn Arg Thr Ala
1               5

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ccccactgtg gggtggaggg gacagata                                        28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
actagggaca ggattggtga cagaaaag                                        28

<210> SEQ ID NO 27
<211> LENGTH: 23
<212> TYPE: DNA
<213> ORGANISM: Unknown
<220> FEATURE:
<223> OTHER INFORMATION: Description of Unknown: Genomic oligonucleotide

```
<400> SEQUENCE: 27
gtcccctcca ccccacagtg ggg                                              23

<210> SEQ ID NO 28
<211> LENGTH: 23
<212> TYPE: DNA
<213> ORGANISM: Unknown
<220> FEATURE:
<223> OTHER INFORMATION: Description of Unknown: Genomic oligonucleotide

<400> SEQUENCE: 28
ggggccacta gggacaggat tgg                                              23

<210> SEQ ID NO 29
<211> LENGTH: 25
<212> TYPE: DNA
<213> ORGANISM: Homo sapiens

<400> SEQUENCE: 29
ctgacctctt ctcttcctcc cacag                                            25

<210> SEQ ID NO 30
<211> LENGTH: 13
<212> TYPE: DNA
<213> ORGANISM: Homo sapiens

<400> SEQUENCE: 30
tttctctcca cag                                                         13

<210> SEQ ID NO 31
<211> LENGTH: 9
<212> TYPE: PRT
<213> ORGANISM: Homo sapiens

<400> SEQUENCE: 31

Leu Ala Gly Leu Ile Asp Ala Asp Gly
1               5
```

DELIVERY METHODS AND COMPOSITIONS FOR NUCLEASE-MEDIATED GENOME ENGINEERING

CROSS-REFERENCE TO RELATED APPLICATIONS

The present application claims the benefit of U.S. Provisional Application No. 61/892,348, filed Oct. 17, 2013 and U.S. Provisional Application No. 62/033,424, filed Aug. 5, 2014, the disclosures of which are hereby incorporated by reference in their entireties.

TECHNICAL FIELD

The present disclosure is in the field of genome engineering, particularly targeted modification of the genome of a cell.

BACKGROUND

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, e.g., U.S. Pat. Nos. 8,586,526; 8,329,986; 8,399,218; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983 and 20130177960 and U.S. application Ser. No. 14/278,903, the disclosures of which are incorporated by reference in their entireties for all purposes.

These methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). Cleavage can occur through the use of specific nucleases such as engineered zinc finger nucleases (ZFN), transcription-activator like effector nucleases (TALENs), using the CRISPR/Cas system with an engineered crRNA/tracr RNA ('single guide RNA') to guide specific cleavage and/or using nucleases based on the Argonaute system (e.g., from *T. thermophilus*, known as 'TtAgo', (Swarts et at (2014) *Nature* 507 (7491): 258-261).

Targeted cleavage using one of the above mentioned nuclease systems can be exploited to insert a nucleic acid into a specific target location using either HDR or NHEJ-mediated processes. However, delivering both the nuclease system and the donor to the cell can be problematic. For example, delivery of a donor or a nuclease via transduction of a plasmid into the cell can be toxic to the recipient cell, especially to a cell which is a primary cell and so not as robust as a cell from a cell line.

CD34+ stem or progenitor cells are a heterogeneous set of cells characterized by their ability to self renew and/or differentiate into the cells of the lymphoid lineage (e.g. T cells, B cells, NK cells) and myeloid lineage (e.g. monocytes, erythrocytes, eosinophiles, basophiles, and neutrophils). Their heterogeneous nature arises from the fact that within the CD34+ stem cell population, there are multiple subgroups which often reflect the multipotency (whether lineage committed) of a specific group. For example, CD34+ cells that are CD38− are more primitive, immature CD34+ progenitor cell, (also referred to as long term hematopoietic progenitors), while those that are CD34+CD38+ (short term hematopoietic progenitors) are lineage committed (see Stella et al (1995) *Hematologica* 80:367-387). When this population then progresses further down the differentiation pathway, the CD34 marker is lost. CD34+ stem cells have enormous potential in clinical cell therapy. However, in part due to their heterogenous nature, performing genetic manipulations such as gene knock out, transgene insertion and the like upon the cells can be difficult. Specifically, these cells are poorly transduced by conventional delivery vectors, the most primitive stem cells are sensitive to modification, there is limited HDR following induced DNA DSBs, and there is insufficient HSC maintenance in prolonged standard culture conditions. Additionally, other cells of interest (for non-limiting example only, cardiomyocytes, medium spiny neurons, primary hepatocytes, embryonic stem cells, induced puripotent stem cells and muscle cells) can be less successfully transduced for genome editing than others.

Thus, there remains a need for compositions and methods for genome engineering to CD34+ cells and other cells of interest that are less toxic and more efficient.

SUMMARY

The present invention describes compositions and methods for use in gene therapy and genome engineering. Specifically, the methods and compositions described relate to introducing nucleic acids into cells such as primary cells including hematopoietic stem cells/progenitor cells (HSC/PC) and T cells. In addition, the methods and compositions of the invention are useful for delivery of AAV particles comprising donor DNAs of interest to such cells.

In some aspects, the invention comprises delivery of at least one nuclease to a cell (e.g., an HSC/PC) for the purpose of genome engineering. In some embodiments, the nuclease is delivered as a peptide, while in others it is delivered as a nucleic acid encoding the nuclease. In some embodiments, more than one nuclease is used. In some preferred embodiments, the nucleic acid encoding the nuclease is an mRNA, and in some instances, the mRNA is protected. The nuclease may comprise a zinc finger nuclease (ZFN), a TALE-nuclease (TALEN) or a CRISPR/Cas or TtAgo nuclease system or a combination thereof. In a preferred embodiment, the nucleic acid encoding the nuclease(s) is delivered via electroporation.

In one aspect, provided herein is a method of integrating one or more transgenes into a genome of an isolated cell, the method comprising sequentially introducing the transgene and at least one nuclease into the cell such that the nuclease mediates targeted integration of the transgene. Thus, in certain A method of integrating one or more transgenes into a genome of an isolated cell, the method comprising: introducing, into the cell, (a) a donor vector comprising the one or more transgenes and (b) at least one nuclease, wherein the at least one nuclease cleaves the genome of the cell such that the one or more transgenes are integrated into the genome of the cell, and further wherein (i) if the donor vector is introduced into the cell before the at least one nuclease, the at least one nuclease is introduced into the cell within 48 hours after donor vector is introduced and; (ii) if the at least one nuclease is introduced before the donor vector, the donor vector is introduced into the cell within 4 hours after the at least one nuclease is introduced. In certain embodiments, the methods can comprise (a) introducing a donor vector comprising the one or more transgenes into the cell; (b) culturing the cell for less than 48 hours (e.g., seconds to 48 hours or any time therebetween); and (c) introducing at least one nuclease into the cell, wherein the at least one nuclease cleaves the genome of the cell such that the one or more transgenes are integrated into the genome of the cell. Alternatively, the methods can comprise: (a) introducing at least one nuclease into the cell; (b) culturing the cell for less than 24 hours (e.g., seconds to 24 hours or any time therebetween); and (c) introducing a donor vector comprising the one or more transgenes into the cell, wherein the at least one nuclease cleaves the genome of the cell such that the one or more transgenes are integrated into the genome of the cell. The method steps may be repeated for integration of additional transgenes into the same and/or different loci. In certain embodiments, the cell is cultured (step (b)) for less than 24 hours (e.g., seconds to 24 hours or any time therebetween). In still further embodiments, the cell is cultured for less than 4 hours, for example, when the nuclease(s) is introduced before introduction of the donor vector.

Any cell can be used, for example, a hematopoietic stem cell (e.g., CD34+ cell) or T-cell (e.g., CD4+ or CD8+ cell). The donor vector may be introduced as a viral or non-viral vector, for example an AAV vector (e.g., AAV6 or AAV6 chimeric vector such as AAV2/6, etc.). The nuclease (e.g., ZFN, TALEN, TtAgo and/or CRISPR/Cas) may also be introduced using viral or non-viral vectors, for example in mRNA form. In certain embodiments, the nuclease targets a safe-harbor gene (e.g., a CCR5 gene, an AAVS1 gene, a Rosa gene, an albumin gene, etc.). The transgene may encode a protein, for example a therapeutic protein that is lacking or deficient in a subject with a disorder (e.g., lysosomal storage disease, hemoglobinopathy, hemophilia, etc.). In certain embodiments, a method of providing one or more proteins to a subject in need thereof is described, the method comprising: introducing one or more transgenes encoding the one or more proteins into an isolated cell according to any of the methods described herein and introducing the cell into the subject such that the one or more proteins are provided to the subject.

In other aspects, the invention comprises delivery of a donor nucleic acid to a target cell. The donor may be delivered prior to, after, or along with the nucleic acid encoding the nuclease(s). In certain embodiments, the donor is delivered simultaneously with the nuclease(s). In other embodiments, the donor is delivered prior to the nuclease(s), including any time before, for example, immediately before, 1 to 60 minutes before (or any time therebetween), 1 to 24 hours before (or any time therebetween), 1 to 48 hours (or any time therebetween) or more than 48 hours before. In certain embodiments, the donor is delivered after the nuclease, preferably within 4 hours. The donor nucleic acid comprises an exogenous sequence (transgene) to be integrated into the genome of the cell, for example, an endogenous locus. The transgene is preferably integrated at or near (e.g., within 1-50 base pairs) of the site of cleavage by the nuclease(s). In some embodiments, the donor comprises a full length gene or fragment thereof flanked by regions of homology with the targeted cleavage site. In some embodiments, the donor lacks homologous regions and is integrated into a target locus through homology independent mechanism (i.e. NHEJ). In other embodiments, the donor comprises an smaller piece of nucleic acid flanked by homologous regions for use in the cell (i.e. for gene correction). In some embodiments, the donor comprises a gene encoding a functional or structural component such as a shRNA, RNAi, miRNA or the like. In other embodiments the donor comprises a gene encoding a regulatory element that binds to and/or modulates expression of a gene of interest.

In other aspects, the donor is delivered by viral and/or non-viral gene transfer methods. In preferred embodiments, the donor is delivered to the cell via an adeno associated virus (AAV). Any AAV vector can be used, including, but not limited to, AAV1, AAV2, AAV3, AAV4, AAV5, AAV6, AAV7, AAV8 and combinations thereof. In some instances, the AAV comprises LTRs that are of a heterologous serotype in comparison with the capsid serotype (e.g., AAV2 ITRs with AAV5, AAV6, or AAV8 capsids). The donor may be delivered using the same gene transfer system as used to deliver the nuclease (including on the same vector) or may be delivered using a different delivery system that is used for the nuclease. In certain embodiments, the donor is delivered using a viral vector (e.g., AAV) and the nuclease(s) is(are) delivered in mRNA form.

The sequence of interest of the donor molecule may comprise one or more sequences encoding a functional polypeptide (e.g., a cDNA), with or without a promoter. In certain embodiments, the nucleic acid sequence comprises a sequence encoding an antibody, an antigen, an enzyme, a growth factor, a receptor (cell surface or nuclear), a hormone, a lymphokine, a cytokine, a reporter, functional fragments of any of the above and combinations of the above. In embodiments in which the functional polypeptide encoding sequences are promoterless, expression of the integrated sequence is then ensured by transcription driven by an endogenous promoter or other control element in the region of interest. In other embodiments, a "tandem" cassette is integrated into the selected site in this manner, the first component of the cassette comprising a promoterless sequence as described above, followed by a transcription termination sequence, and a second sequence, encoding an autonomous expression cassette. Additional sequences (coding or non-coding sequences) may be included in the donor molecule between the homology arms, including but not limited to, sequences encoding a 2A peptide, SA site, IRES, etc.

In another aspect, described herein are methods of integrating a donor nucleic acid into the genome of a cell via homology-independent mechanisms. The methods comprise creating a double-stranded break (DSB) in the genome of a cell and cleaving the donor molecule using a nuclease, such that the donor nucleic acid is integrated at the site of the DSB. In certain embodiments, the donor nucleic acid is integrated via non-homology dependent methods (e.g., NHEJ). As noted above, upon in vivo cleavage the donor sequences can be integrated in a targeted manner into the genome of a cell at the location of a DSB. The donor sequence can include one or more of the same target sites for one or more of the nucleases used to create the DSB. Thus, the donor sequence may be cleaved by one or more of the same nucleases used to cleave the endogenous gene into which integration is desired. In certain embodiments, the donor sequence includes different nuclease target sites from the nucleases used to induce the DSB. DSBs in the genome of the target cell may be created by any mechanism. In certain embodiments, the DSB is created by one or more zinc-finger nucleases (ZFNs), fusion proteins comprising a zinc finger binding domain, which is engineered to bind a sequence within the region of interest, and a cleavage domain or a cleavage half-domain. In other embodiments, the DSB is created by one or more TALE DNA-binding domains (naturally occurring or non-naturally occurring) fused to a nuclease domain (TALEN). In yet further embodiments, the DSB is created using a CRISPR/Cas or TtAgo nuclease system where an engineered single guide RNA or its functional equivalent is used as needed to guide the nuclease to a targeted site in a genome.

In other aspects, the nuclease(s) binds to and/or cleaves a safe-harbor gene, for example a CCR5 gene, a PPP1R12C (also known as AAVS1) gene, a Rosa gene or an albumin gene in mammalian cells. In addition, to aid in selection in mammalian systems, the HPRT locus may be used.

In one aspect, the donor is a regulatory protein of interest (e.g. ZFP TFs, TALE TFs or a CRISPR/Cas TF) that binds to and/or modulates expression of a gene of interest. In one embodiment, the regulatory proteins bind to a DNA sequence and prevent binding of other regulatory factors. In another embodiment, the binding of a the regulatory protein may modulate (i.e. induce or repress) expression of a target DNA.

In other aspects, provided herein is a cell which has been genetically modified (e.g., transgenic) as described herein, for example using a nuclease to introduce the genetic modification. In certain embodiments, the cell is made by the methods described herein. In certain embodiments, the cell comprises a transgene that is integrated into a safe-harbor locus, such as CCR5, AAVS1, ALB, Rosa26 and/or HPRT. The cells comprising the integrated transgene may express the transgene from an endogenous promoter or, alternatively, the transgene may include regulatory and control elements such as exogenous promoters that drive expression of the transgene (e.g., when integrated into a safe harbor locus). In certain embodiments, the cells comprising the transgene do not include any viral vector sequences integrated into the genome. The cells may be any eukaryotic cell, for example CD34+ stem cells (e.g., patient-derived stem cells mobilized in patients from the bone marrow into the peripheral blood via granulocyte colony-stimulating factor (GCSF) or other mobilizing agent administration or harvested directly from the bone marrow or umbilical cords). The cells can be harvested, purified, cultured, and the nucleases and/or donor introduced into the cell by any suitable method.

Compositions such as pharmaceutical compositions comprising the genetically modified cells as described herein are also provided. In some embodiments, the compositions comprise CD34+ HSC/PC or HSC/PC cell population. In other embodiments, the compositions comprise T cells (e.g. CD4+ and/or CD8+ T cells). In still further embodiments, the T cell compositions comprise only CD4+ or only CD8+ cells.

In another aspect, provided are methods of using the genetically modified cells as described herein. In certain embodiments, genetically modified blood cell precursors ("HSC/PC") are given in a bone marrow transplant and the HSC/PC differentiate and mature in vivo. In some embodiments, the HSC/PC are isolated following G-CSF-induced mobilization, and in others, the cells are isolated from human bone marrow or umbilical cords. In some aspects, the HSC/PC are edited by treatment with a nuclease designed to knock out a specific gene or regulatory sequence. In other aspects, the HSC/PC are modified with an engineered nuclease and a donor nucleic acid such that a wild type gene or other gene of interest is inserted and expressed and/or an endogenous aberrant gene is corrected. In some embodiments, the modified HSCs/PC are administered to the patient following mild myeloablative pre-conditioning. In other aspects, the HSC/PC are administered after full myeloablation such that following engraftment, 100% of the hematopoietic cells are derived from the modified HSC/PC. Furthermore, the cell may be arrested in the G2 phase of the cell cycle.

In some embodiments, the transgenic HSC/PC cell and/or animal includes a transgene that encodes a human gene. In some instances, the transgenic animal comprises a knock out at the endogenous locus corresponding to exogenous transgene, thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., safe-harbor) into a stem cell (e.g., an embryonic stem cell, an induced pluripotent stem cell, a hematopoietic stem or precursor cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

A kit, comprising the AAVs and nucleic acids of the invention, is also provided. The kit may comprise nucleic acids encoding the nucleases, (e.g. RNA molecules or ZFN, TALEN, TtAgo or CRISPR/Cas system encoding genes contained in a suitable expression vector), or aliquots of the nuclease proteins, donor molecules, suitable stemness modifiers, instructions for performing the methods of the invention, and the like. The kit may also comprise donor molecules of interest such as selection or screening markers.

These and other aspects will be readily apparent to the skilled artisan in light of disclosure as a whole.

BRIEF DESCRIPTION OF THE DRAWINGS

FIG. 1A depicts GFP expression in mobilized peripheral blood CD34+ cells (mPBCD34+) that were transduced with the indicated AAV vectors containing a CMV-driven eGFP transgene. Data shown in FIG. 1A is from cells 2 days post transduction. Cells were then collected at 2 and 5 days post-infection (dpi) and analyzed using a flow cytometer (Guava, Millipore). FIG. 1B depicts the percent of cells in each population that are GFP positive.

FIGS. 2A to 2C depict ZFN-mediated AAV donor insertion into CD34+ cells. FIG. 2A depicts a schematic representation of the AAV6-R5-160-XhoI donor construct used in this study. The AAV6 used in these studies was a pseudotyped virus comprising AAV2 ITRs and AAV6 capsids (i.e. "AAV2/6"). The donor DNA is constructed between the AAV2 left ITR (L-ITR) and right ITR (R-ITR), in which a XhoI site is introduced between the CCR5-specific ZFN binding sites. The CCR5 left arm and right arm indicate sequences derived from the genomic sequence of the CCR5 locus flanking the CCR5 ZFN binding sites. The second XhoI site (to the left of the CCR5 left homology arm in FIG. 2A) will not be integrated following donor integration by virtue of its being outside the homology arm. FIGS. 2B and 2C depict CD34+ cells transduced with the AAV6-R5-160-XhoI donor at doses between 300-1e5 vg/cell, followed by introduction by electroporation using a BTX ECM830 (Harvard Apparatus) of CCR5-specific ZFN mRNA (120 ug/ml) 24 hours after transduction. Cells were collected at 5 dpi for genomic DNA (gDNA) purification and processed for the subsequent RFLP assay depicted in FIG. 2B and Illumina deep sequencing depicted in FIG. 2C. The wild type (undigested DNA) and RFLP bands are indicated by arrows in FIG. 2B as is the percent of RFLP detected. FIG. 2C is a graph depicting the percent of genome modification or indels found by the Illumina deep sequencing.

FIGS. 3A and 3B are both graphs showing the amount of genome modification detected by Illumina deep sequencing: either insertions or deletions ("indels"), or targeted integration (TI) of the RFLP provided by the donor molecule at the indicated time points.

FIGS. 4A to 4D show results of CD34+ modified by ZFNs and AAV donors. FIG. 4A depicts a schematic representation of the R5-pgk-GFP-pA donor construct used in this study. The donor DNA is constructed between the AAV2 L-ITR and R-ITR, in which a PGK promoter-driven eGFP expression cassette (1.6 kb) was inserted between the CCR5 ZFN binding sites. The CCR5 left arm and right arm indicate sequences derived from the genomic sequence of the CCR5 locus flanking the CCR5 ZFN binding sites. FIG. 4B depicts the results of flow cytometry analysis of CD34+ cells that were transduced with the AAV6-R5-pgk-GFP-pA donor at doses between 300-3e3 vg/cell. CCR5-specific ZFN mRNA (120 ug/ml) was introduced into transduced cells 24 hours later by electroporation using a BTX ECM830 (Harvard Apparatus). Cells were collected for flow cytometry analysis at 15 dpi. Numbers in the lower left quadrant of the graphs indicate percentage of eGFP+ cells present in the live cell population (PI−). FIG. 4C depicts a gel showing the detection of targeted integration of the GFP cassette into the CCR5 locus using a semi-quantitative 'In-Out' PCR assay. A set of standard controls was prepared by serial dilution of a genomic DNA pool of known frequency of GFP transgene integration at the CCR5 locus (determined by Southern blot) with unmodified wild-type genomic DNA. PCR was performed using equal amount of genomic DNA and a primer present in the polyA region (present in the eGFP cassette) and a primer located outside of the CCR5 homologous arm region at the 3' side of the ZFN target sites. FIG. 4D depicts a gel showing the results using a second set of PCR reactions utilizing one additional primer pair such that both primers in this pair were at the 5' side of the target sites and one of which is located outside of the CCR5 homologous region. This second pair was included in the same PCR reactions as in FIG. 2C such that there were two primer pairs present. The second primer pair was used as a measurement of genomic DNA input. GFP-TI-specific PCR products and the non-TI-specific PCR products (total) are indicated by arrows.

FIG. 5A depicts a schematic representation of the AAVS1-HindIII donor used in this study. The donor DNA was inserted between the AAV2 L-ITR and R-ITR, in which a HindIII site was introduced between the binding sites of an AAVS1-specific ZFN pair. The AAVS1 left arm and right arm indicate homology arm sequences derived from the genomic sequence of the AAVS1 locus flanking the AAVS1 ZFN binding sites. FIG. 5B depicts a graph of CD34+ cells that were transduced with the AAV6-AAVS1-HindIII donor at 1000 or 3000 vg/ml. AAVS1 ZFN mRNA (40 ug/ml) was introduced into transduced cells 24 hours later by electroporation using a BTX ECM830 (Harvard Apparatus). Cells were collected at 5 dpi for genomic DNA (gDNA) purification and processed for subsequent Illumina deep sequencing. The graph depicts the amount of genomic modification as measured either by indel formation or targeted integration.

FIG. 7A shows the percentage of genomic modification, both targeted integration ("TI") and insertions/deletions ("indels") under the indicated conditions. FIG. 7B shows the percentage of targeted integration ("% TI") under the indicated conditions.

FIGS. 8A and 8B depicting results of nuclease-mediated integration into CD4+ primary T cells. FIG. 8A shows the percentage of genomic modification of CCR5, both targeted integration ("TI") and insertions/deletions ("indels"), following introduction of CCR5-specific ZFN and an AAV2, AAV6 or IDLV comprising donor under the indicated conditions. FIG. 8B shows the percentage of genomic modification of AAVS1, both targeted integration ("TI") and insertions/deletions ("indels"), following introduction of AAVS1 nucleases and an AAV6 donor under the indicated conditions. Increased TI is observed with the use of the AAV6 donor as compared to the AAV2 or IDLV donor under these conditions.

FIGS. 9A and 9B depict results of nuclease-mediated integration into CD8+ primary T cells. FIG. 9A shows the percentage of genomic modification of CCR5, both targeted integration ("TI") and insertions/deletions ("indels"), following introduction of CCR5-specific ZFN and an AAV2, AAV6 or IDLV comprising donor under the indicated conditions. FIG. 9B shows the percentage of genomic modification of AAVS1, both targeted integration ("TI") and insertions/deletions ("indels"), following introduction of AAVS1 nucleases and an AAV6 donor under the indicated conditions. Increased TI is observed with the use of the AAV6 donor as compared to the AAV2 or IDLV donor under these conditions.

DETAILED DESCRIPTION

Figure 1A:
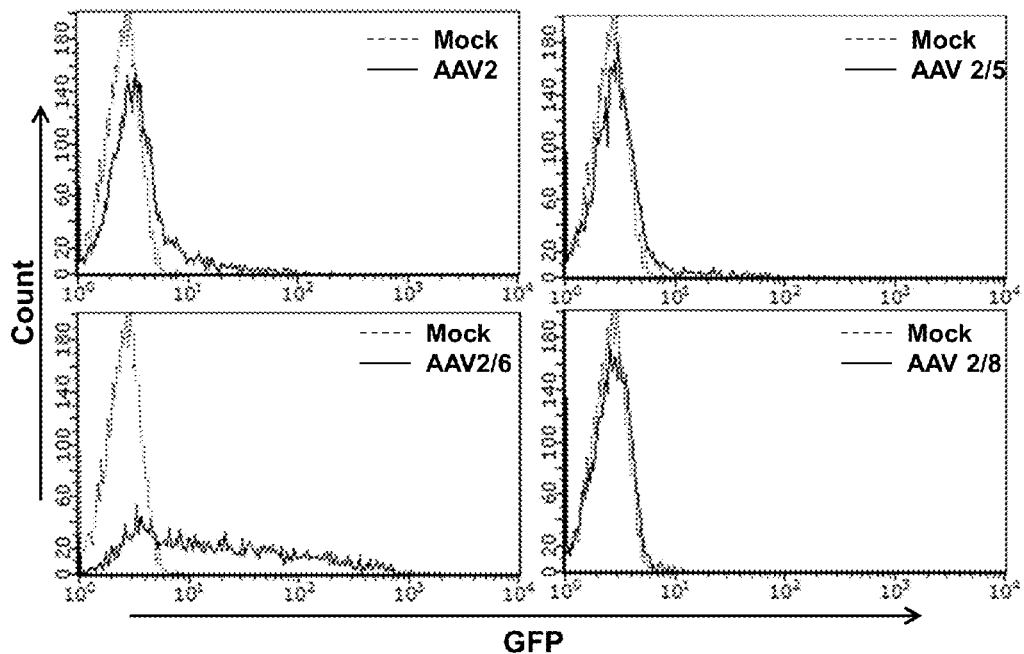
FIGS. 1A and 1B depict GFP expression in ZFN-AAV modified CD34+ cells.

Disclosed herein are compositions and methods for transduction of a cell for use in gene therapy or genome engineering. In particular, nuclease-mediated (i.e. ZFN, TALEN, TtAgo or CRISPR/Cas system) targeted integration of an exogenous sequence or genome alteration by targeted cleavage followed by non-homologous end joining, is efficiently achieved in a cell. Particularly useful for transduction and engineering of HSC/PC and T cells, however, the methods and compositions can also be used for other cell types.

Delivery of ZFNs and donor template DNA was optimized as detailed and cell types include any hematopoietic stem cell or precursor cell, including CD34+ cells. CD34+ cells can include primitive (CD133+CD90+, or CD90−), early (CD34+, CD133+) and committed (CD34+CD133−) CD34+ subsets as well as T cells. The methods described herein result in long-term multilineage engraftment in animals treated with the modified cells.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,586,526; 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789, 538; 5,925,523; 6,007,988; 6,013,453; 6,200,759; WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. (See, e.g., Swarts et al, ibid, G. Sheng et al., (2013) *Proc. Natl. Acad. Sci. U.S.A.* 111, 652). A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins or TALEN can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 2008/0131962 and 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 100 and 5,000 nucleotides in length (or any value therebetween) and even more preferable, between about 100 and 2,000 base pairs (or any value therebetween).

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity using standard techniques. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods known in the art. Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, biopolymer nanoparticle delivery (see Nitta and Numata (2013) $Int\ J\ Mol\ Sci$ 14:1629), calcium phosphate co-precipitation, DEAE-dextran-mediated transfer and viral vector-mediated transfer. An exogeneous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Secretory tissues" are those tissues in an animal that secrete products out of the individual cell into a lumen of some type which are typically derived from epithelium. Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues include individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP, TALE or Cas DNA-binding domain and the activation domain are in operative linkage if, in the fusion polypeptide, the ZFP, TALE of Cas DNA-binding domain portion is able to bind its target site and/or its binding site, while the activation domain is able to upregulate gene expression. When a fusion polypeptide in which a ZFP, TALE or Cas DNA-binding domain is fused to a cleavage domain, the ZFP, TALE or Cas DNA-binding domain and the cleavage domain are in operative linkage if, in the fusion polypeptide, the ZFP, TALE or Cas DNA-binding domain portion is able to bind its target site and/or its binding site, while the cleavage domain is able to cleave DNA in the vicinity of the target site (e.g., 1 to 500 base pairs or any value therebetween on either side of the target site).

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci in mammalian cells are the AAVS1 gene (U.S. Pat. No. 8,110,379), the CCR5 gene (U.S. Publication No. 20080159996), the Rosa locus (WO 2010/065123) and/or the albumin locus (U.S. Publication Nos. 20130177960 and 20130177983). A safe harbor in a plant cell is the ZP15 locus (U.S. patent publication 20100199389).

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the or stem cells of the invention can be administered. Subjects of the present invention include those that have been exposed to one or more chemical toxins, including, for example, a nerve toxin.

"Stemness" refers to the relative ability of any cell to act in a stem cell-like manner, i.e., the degree of toti-, pluri-, or oligopotentcy and expanded or indefinite self renewal that any particular stem cell may have.

Nucleases

Described herein are compositions, particularly nucleases, such as ZFNs, TALEs, homing endonucleases, Ttago and/or CRISPR/Cas systems, that are useful for in vivo cleavage of a donor molecule carrying a transgene and nucleases for cleavage of the genome of a cell such that the transgene is integrated into the genome in a targeted manner.

In certain embodiments, one or more of the nucleases are naturally occurring. In other embodiments, one or more of the nucleases are non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains). In other embodiments, the nuclease comprises a system such as the CRISPR/Cas or Ttago system.

A. DNA-Binding Domains

In certain embodiments, the composition and methods described herein employ a meganuclease (homing endonuclease) DNA-binding domain for binding to the donor molecule and/or binding to the region of interest in the genome of the cell.

Naturally-occurring meganucleases recognize 15-40 base-pair cleavage sites and are commonly grouped into four families: the LAGLIDADG (SEQ ID NO: 31) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

In certain embodiments, the methods and compositions described herein make use of a nuclease that comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of Xanthomonas depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). See, e.g., U.S. Pat. No. 8,586,526; Christian et al ((2010)<*Genetics* epub 10.1534/genetics.110.120717).

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; and WO 01/88197. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 8,772,453; 6,479,626; 6,903,185; and 7,153,949 for exemplary linker sequences. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,815; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding domain is part of a CRISPR/Cas nuclease system. See, e.g., U.S. Pat. No. 8,697,359 and U.S. patent application Ser. No. 14/278,903. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoSComput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus*, *Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celcius. Ago-RNA-mediated DNA cleavage could be used to effect a panopoly of outcomes including gene knock-out, targeted gene addition, gene correction, targeted gene deletion using techniques standard in the art for exploitation of DNA breaks.

Thus, the nuclease comprises a DNA-binding domain in that specifically binds to a target site in any gene into which it is desired to insert a donor (transgene).

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Natl Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014, 275. Likewise, TALE DNA-binding domains have been fused to nuclease domains to create TALENs. See, e.g., U.S. Pat. No. 8,586,526.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Pat. No. 7,888,121, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 8,772,453; 8,623,618; 8,409,861; 8,034,598; 7,914, 796; and 7,888,121, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Pat. Nos. 7,914,796 and 8,034,598, the disclosures of which are incorporated by reference in their entireties for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. No. 8,772,453. In other embodiments, the engineered cleavage half domain comprises the "Sharkey" and/or "Sharkey'" mutations (see Guo et al, (2010) *J. Mol. Biol.* 400 (1):96-107).

Engineered cleavage half-domains described herein can be prepared using any suitable method, for example, by site-directed mutagenesis of wild-type cleavage half-domains (Fok I) as described in U.S. Pat. Nos. 8,772,453; 8,623,618; 8,409,861; 8,034,598; 7,914,796; and 7,888,121.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314.

Expression of the nuclease may be under the control of a constitutive promoter or an inducible promoter, for example the galactokinase promoter which is activated (de-repressed) in the presence of raffinose and/or galactose and repressed in presence of glucose.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Target Sites

As described in detail above, DNA domains can be engineered to bind to any sequence of choice. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Pat. No. 8,586,526.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Pat. No. 8,586,526.

Non-limiting examples of suitable target genes include a beta (β) globin gene (HBB), a gamma (δ) globin gene (HBG1), a B-cell lymphoma/leukemia 11A (BCL11A) gene, a Kruppel-like factor 1 (KLF1) gene, a CCR5 gene, a CXCR4 gene, a PPP1R12C (AAVS1) gene, an hypoxanthine phosphoribosyltransferase (HPRT) gene, an albumin gene, a Factor VIII gene, a Factor IXgene, a Leucine-rich repeat kinase 2 (LRRK2) gene, a Hungtingin (Htt) gene, a rhodopsin (RHO) gene, a Cystic Fibrosis Transmembrane Conductance Regulator (CFTR) gene, a surfactant protein B gene (SFTPB), a T-cell receptor alpha (TRAC) gene, a T-cell receptor beta (TRBC) gene, a programmed cell death 1 (PD1) gene, a Cytotoxic T-Lymphocyte Antigen 4 (CTLA-4) gene, an human leukocyte antigen (HLA) A gene, an HLA B gene, an HLA C gene, an HLA-DPA gene, an HLA-DQ gene, an HLA-DRA gene, a LMP7 gene, a Transporter associated with Antigen Processing (TAP) 1 gene, a TAP2 gene, a tapasin gene (TAPBP), a class II major histocompatibility complex transactivator (CIITA) gene, a dystrophin gene (DMD), a glucocorticoid receptor gene (GR), an IL2RG gene, a Rag-1 gene, an RFX5 gene, a FAD2 gene, a FAD3 gene, a ZP15 gene, a KASII gene, a MDH gene, and/or an EPSPS gene.

In certain embodiments, the nuclease targets a "safe harbor" loci such as the AAVS1, HPRT, albumin and CCR5 genes in human cells, and Rosa26 in murine cells (see, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960) and the Zp15 locus in plants (see U.S. Pat. No. 8,329,986).

Donors

The present disclosure relates to nuclease-mediated targeted integration of an exogenous sequence into the genome of an HSC/PC. As noted above, insertion of an exogenous sequence (also called a "donor sequence" or "donor" or "transgene"), for example for correction of a mutant gene or for increased expression of a wild-type gene or for expression of a transgene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

Described herein are methods of targeted insertion of any polynucleotides for insertion into a chosen location. Polynucleotides for insertion can also be referred to as "exogenous" polynucleotides, "donor" polynucleotides or molecules or "transgenes." The donor polynucleotide can be DNA, single-stranded and/or double-stranded and can be introduced into a cell in linear or circular form. See, e.g., U.S. Patent Publication Nos. 20100047805 and 20110207221. The donor sequence(s) can also be introduced in DNA MC form, which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. If introduced in double-stranded form, the donor may include one or more nuclease target sites, for example, nuclease target sites flanking the transgene to be integrated into the cell's genome. See, e.g., U.S. Patent Publication No. 20130326645.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome, nanoparticle or poloxamer, or can be delivered by viruses (e.g., adenovirus, AAV, herpesvirus, retrovirus, lentivirus and integrase defective lentivirus (IDLV)).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 2 target sites, for example for a pair of ZFNs or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted (e.g., globin, AAVS1, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In other embodiments, the transgene (e.g., with or without peptide-encoding sequences) is integrated into any endogenous locus, for example a safe-harbor locus. See, e.g., US patent publications 20080299580; 20080159996 and 201000218264.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals. Additionally, splice acceptor sequences may be included. Exemplary splice acceptor site sequences are known to those of skill in the art and include, by way of example only, CTGACCTCTTCTCTTCCTCCCACAG, (SEQ ID NO:29) (from the human HBB gene) and TTTCTCTCCACAG (SEQ ID NO:30) (from the human Immunoglobulin-gamma gene).

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs or fragments thereof), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs. The exogenous sequences may also be a fragment of a transgene for linking with an endogenous gene sequence of interest. For example, a fragment of a transgene comprising sequence at the 3' end of a gene of interest may be utilized to correct, via insertion or replacement, of a sequence encoding a mutation in the 3' end of an endogenous gene sequence. Similarly, the fragment may comprise sequences similar to the 5' end of the endogenous gene for insertion/replacement of the endogenous sequences to correct or modify such endogenous sequence. Additionally the fragment may encode a functional domain of interest (catalytic, secretory or the like) for linking in situ to an endogenous gene sequence to produce a fusion protein.

For example, the exogenous sequence may comprise a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type Factor IX gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

The donor(s) may be delivered prior to, simultaneously or after the nuclease(s) is(are) introduced into a cell. In certain embodiments, the donor(s) are delivered simultaneously with the nuclease(s). In other embodiments, the donors are delivered prior to the nuclease(s), for example, seconds to hours to days before the donors, including, but not limited to, 1 to 60 minutes (or any time therebetween) before the nuclease(s), 1 to 24 hours (or any time therebetween) before the nuclease(s) or more than 24 hours before the nuclease(s). In certain embodiments, the donor is delivered after the nuclease, preferably within 4 hours.

The donors may be delivered using the same delivery systems as the nuclease(s). When delivered simultaneously, the donors and nucleases may be on the same vector, for example an AAV vector (e.g., AAV6). In certain embodiments, the donors are delivered using an AAV vector and the nuclease(s) are delivered in mRNA form.

Cells

Thus, provided herein are genetically modified cells, for example primary HSC/PC or T cells comprising a transgene, including a transgene that expresses a functional protein in the cell. Cells produced by the methods described herein are also provided. The transgene is integrated in a targeted manner into the cell's genome using one or more nucleases. In certain embodiments, the transgene is integrated into a safe harbor gene.

Unlike random integration, targeted integration ensures that the transgene is integrated into a specified gene or locus. The transgene may be integrated anywhere in the target gene. In certain embodiments, the transgene is integrated at or near the nuclease cleavage site, for example, within 1-300 (or any value therebetwen) base pairs upstream or downstream of the site of cleavage, more preferably within 1-100 base pairs (or any value therebetween) of either side of the cleavage site, even more preferably within 1 to 50 base pairs (or any value therebetween) of either side of the cleavage site. In certain embodiments, the integrated sequence comprising the transgene does not include any vector sequences (e.g., viral vector sequences).

Any cell type can be genetically modified as described herein, including but not limited to cells and cell lines. Other non-limiting examples of cells as described herein include T-cells (e.g., CD4+, CD3+, CD8+, etc.); dendritic cells; B-cells; autologous (e.g., patient-derived) or heterologous pluripotent, totipotent or multipotent stem cells (e.g., CD34+ cells, induced pluripotent stem cells (iPSCs), embryonic stem cells or the like). In certain embodiments, the cells as described herein are CD34+ cells derived from a patient with a disorder it is desired to treat.

The cells as described herein are useful in treating and/or preventing a disorder, for example, by ex vivo therapies. The nuclease-modified cells can be expanded and then reintroduced into the patient using standard techniques. See, e.g., Tebas et al (2014) *New Eng J Med* 370 (10):901. In the case of stem cells, after infusion into the subject, in vivo differentiation of these precursors into cells expressing the functional transgene also occurs. Pharmaceutical compositions comprising the cells as described herein are also provided. In addition, the cells may be cryopreserved prior to administration to a patient.

Delivery

The nucleases, polynucleotides encoding these nucleases, donor polynucleotides and compositions comprising the proteins and/or polynucleotides described herein may be delivered in vivo or ex vivo by any suitable means into any cell type.

Suitable cells include eukaryotic (e.g., animal) and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO, MDCK or HEK293 cell line. Suitable cells also include stem cells such as, by way of example, embryonic stem cells, induced pluripotent stem cells, hematopoietic stem cells, neuronal stem cells and mesenchymal stem cells.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the ZFN(s), TALEN(s) or CRIPSR/Cas systems. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors (DNA MC(s)). When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA or RNA plasmids, DNA MCs, naked nucleic acid, and nucleic acid complexed with a delivery vehicle such as a liposome, nanoparticle or poloxamer. Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51 (1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, other nanoparticle, polycation or lipid:nucleic acid conjugates, naked DNA, artificial virions, and agent-enhanced uptake of DNA. Sonoporation using, e.g., the Sonitron 2000 system (RichMar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27 (7):643).

The use of RNA or DNA viral based systems for the delivery of nucleic acids encoding engineered ZFPs, TALEs and/or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh.10 and any novel AAV serotype can also be used in accordance with the present invention. In some embodiments, chimeric AAV is used where the viral origins of the LTR sequences of the viral nucleic acid are heterologous to the viral origin of the capsid sequences. Examples include chimeric virus with LTRs derived from AAV2 and capsids derived from AAV5, AAV6, AAV8 or AAV9 (i.e. AAV2/5, AAV2/6, AAV2/8 and AAV2/9, respectively).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:15-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package AAV and adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. In some embodiments, AAV is produced using a baculovirus expression system.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding and/or double-stranded donors) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, the nucleases and donors can be carried by the same DNA MC. Alternatively, a donor polynucleotide can be carried by a MC, while the one or more nucleases can be carried by a standard plasmid or AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of diseases and conditions that are amenable to insertion of a transgenes encoding a therapeutic protein, for example treatment of hemophilias via nuclease-mediated integration of clotting factors such as Factor VIII (F8). The compositions are administered to a human patient in an amount effective to obtain the desired concentration of the therapeutic polypeptide in the serum or the target organ or cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics*, 6:335-341.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.*, 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

The following Examples relate to exemplary embodiments of the present disclosure in which the nuclease comprises a zinc finger nuclease (ZFN), a TALEN or a CRISPR/Cas nuclease system. It will be appreciated that this is for purposes of exemplification only and that other nucleases can be used, for instance Ttago systems, homing endonucleases (meganucleases) with engineered DNA-binding domains and/or fusions of naturally occurring of engineered homing endonucleases (meganucleases) DNA-binding domains and heterologous cleavage domains and/or fusions of meganucleases and TALE proteins.

EXAMPLES

Example 1

Assembly of Zinc Finger Nucleases

ZFNs were assembled against the human CCR5 and AAVS1 genes and were tested by ELISA and CELL assays as described in Miller et al. (2007) *Nat. Biotechnol.* 25:778-785. For CCR5-specific ZFNs, see U.S. Pat. No. 7,951,925 and for AAVS1-specific ZFNs, see U.S. Pat. No. 8,110,379, both incorporated by reference herein.

Example 2

Delivery of AAV-GFP Donor to CD34+ Cells

To test AAV as a vehicle for delivery of donor molecules to CD34+ cells four different AAV serotypes were evaluated. The AAV vectors were constructed carrying a CMV-driven eGFP transgene inserted between the serotype specific LTRs. The AAV serotypes tested including AAV2/5, AAV2/6, AAV2/8 and AAV2. In these AAV vectors, all the ZFN encoding nucleic acid sequence is flanked by the AAV2 ITRs, and then encapsulated using capsid proteins from AAV5, 6, or 8, respectively. (see Grimm and Kay (2003) *Current Gene Therapy* 3: 281-304).

Production of the donor containing virus particles was done by preparation using a HEK293 system using standard methods in the art (See Li et al, ibid, see e.g. U.S. Pat No.6,723,551). Mobilized peripheral blood CD34+ cells (mPBCD34+), which are from G-CSF mobilized leukapheresis and purified by positive selection using the Milenyi CliniMA CS system (Miltenyi Biotech, Germany) were transduced with the indicated AAV vectors containing the CMV-driven eGFP transgene by culturing the cells in the presence of AAV vectors. Cells were then collected at 2 and 5 days post-infection (dpi) and analyzed for GFP expression using a flow cytometer (Guava, Millipore) according to manufacturer's protocols.

Figure 1B:
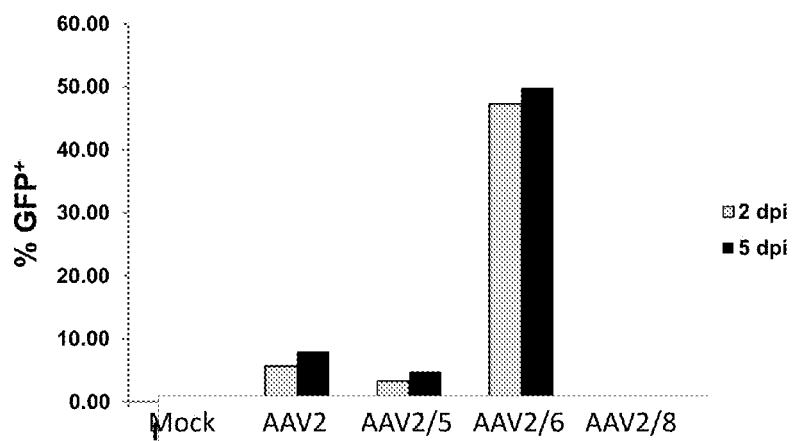

The results as shown in FIG. 1 demonstrated that the AAV2/6—GFP donor particles were able to generate more than 6-fold more GFP expressing CD34+ HSC/PC than cells tranduced with the other AAV serotypes in these conditions.

Example 3

Delivery of a RFLP-Carrying Transgene Using AAV2/6

To test targeted integration in CD34+ cells, an AAV6-R5-160-XhoI donor was generated. In the transgene insert in this viral vector, a XhoI restriction enzyme site was introduced between two CCR5-specific ZFN binding sites (FIG. 2A), ZFN pair 8267:20505 (also referred to as 8196z). The XhoI site is flanked by homology arms whose sequence is homologous to regions in the genome that flank the ZFN cleavage site in the genome. Specifically, the right homology arm is approximately 1351 base pairs while the left homology arm is approximately 509 base pairs. The AAV6-R5-160-XhoI donor was transduced into CD34+ cells as described above at doses between 300-1e5 vg/cell. A day later, mRNA encoding CCR5-specific ZFN (120 µg/ml) was introduced into transduced cells by electroporation using a BTX ECM830 (Harvard Apparatus). The mRNA manufactured by Asuragen (Austin, Tex.) as a 2A construct (8267-2A-2050) and was used at 120 ug/ml.

Cells were collected at 5 days post-infection (dpi) for genomic DNA (gDNA) purification and processed for subsequent RFLP assay (FIG. 2B) and Illumina deep sequencing (FIG. 2C). Genomic DNA was isolated using a Nucleo-Spin Tissue XS kit (Macherey-Nagel, Bethlehem, Pa.). The RFLP assay was performed using a nested PCR approach where the region surrounding the ZFN cleavage site was first amplified using the following primers: 5'-CTGTGCT-TCAAGGTCCTTGTCTGC-3' (SEQ ID NO:1) and 5'-CTCTGTCTCCTTCTACAGCCAAGC-3' (SEQ ID NO:2). The PCR products were gel purified and PCR amplified again with the following primer pair: 5'-AAGATGGATTATCAAGTGTCAAGTCC-3' (SEQ ID NO:3) and 5'-CAAAGTCCCACTGGGCG-3' (SEQ ID NO:4).

The amplified DNA was then subject to restriction analysis with XhoI and the products were analyzed by gel electrophoresis. As shown in FIG. 2B, the analysis demonstrated the presence of the XhoI containing transgene at levels of up to approximately 18 percent of the DNA molecules present, but only in CD34+ samples that had been treated with both the AAV6 donor and the mRNA encoding the CCR5-specific ZFN.

Illumina deep sequencing allowed the simultaneous detection of ZFN-induced genome modification by the NHEJ (typically small insertions and/or deletions known as "indels") and HDR (TI) pathways (FIG. 2C). Briefly, the region surrounding the CCR5 ZFN cleavage site was first amplified using primers located outside of the homologous arms, which are as the following: 5'-CTGTGCT-TCAAGGTCCTTGTCTGC-3' (SEQ ID NO:1) and 5'-CTCTGTCTCCTTCTACAGCCAAGC-3' (SEQ ID NO:2). The PCR products were gel purified and then PCR amplified using a pair of fused primers, which contain both target-specific sequences and adaptors for Illumina-deep sequencing: 5'-ACACTCTTTCCCTACACGACGCTCT-TCCGATCTNNNNNGCCAGGTTGAGCAG GTAGATG-3' (SEQ ID NO:5) and 5'-AGACGTGTGCTCTTC-CGATCTGCTCTACTCACTGGTGTTCATCTTT-3' (SEQ ID NO:6). Lastly, sample barcodes were added in a final PCR reaction using the following primer pair: 5'-AATGA-TACGGCGACCACCGAGATCTACACNNNNNNNNA-CACTCTTTCCCTAC ACGACGCTCTT-3' (SEQ ID NO:7) and 5'-CAAGCAGAAGACGGCATACGA-GATNNNNNNNNGTGACTGGAGTTCAGACGT GTGCTCTTCCGATCT-3' (SEQ ID NO:8). The final PCR products were run in a MiSeq system (Illumina, San Diego, Calif.). Data were analyzed using a customized script.

An AAV6 donor dose-dependent increase of TI frequencies was observed. Peak level of TI (22%) was achieved at 10,000 vg/ml of AAV6 donor (FIG. 2C). In addition, indel frequence exhibited an inverted correlation with the doses of AAV6 donor and TI frequencies.

Example 4

Optimization of Timing and Order of Donor and ZFN Treatment

The optimal timing and order of AAV6 transduction and ZFN mRNA electroporation were examined to maximize targeted integration of the transgene by HDR. AAV6-R5-

160-XhoI donor was introduced into CD34+ cells up to 48 hours before (−48 hr) to 20 hours after (+20 hr) electroporation (EP) with the CCR5-specific ZFN mRNA. Cells were collected and processed at a later time point for gDNA purification and subsequent Illumina deep sequencing.

Figure 3A:
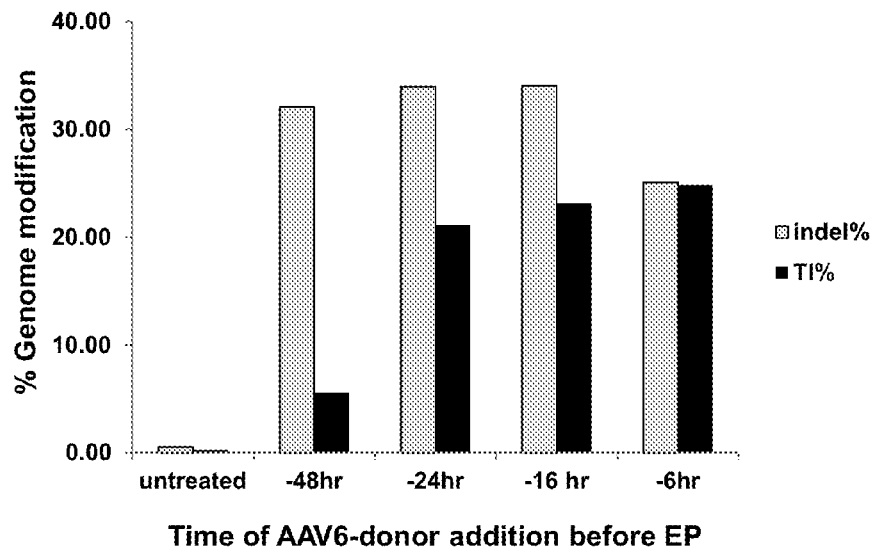
FIGS. 3A and 3B are graphs depicting nuclease-modification in response to the timing and order of nuclease and donor administration. AAV6-R5-160-XhoI donor was introduced up to 48 hours before (−48 hours) to 20 hours after (+20 hours) electroporation (EP) of CD34+ cells with the CCR5-specific ZFN mRNA using a BTX ECM830 (Harvard Apparatus) (−48 hr to −6 hr in FIG. 3A and −20 hr to +20 hr in FIG. 3B). Cells were collected later for genomic DNA (gDNA) purification and processed for subsequent Illumina deep sequencing.
Figure 3B:
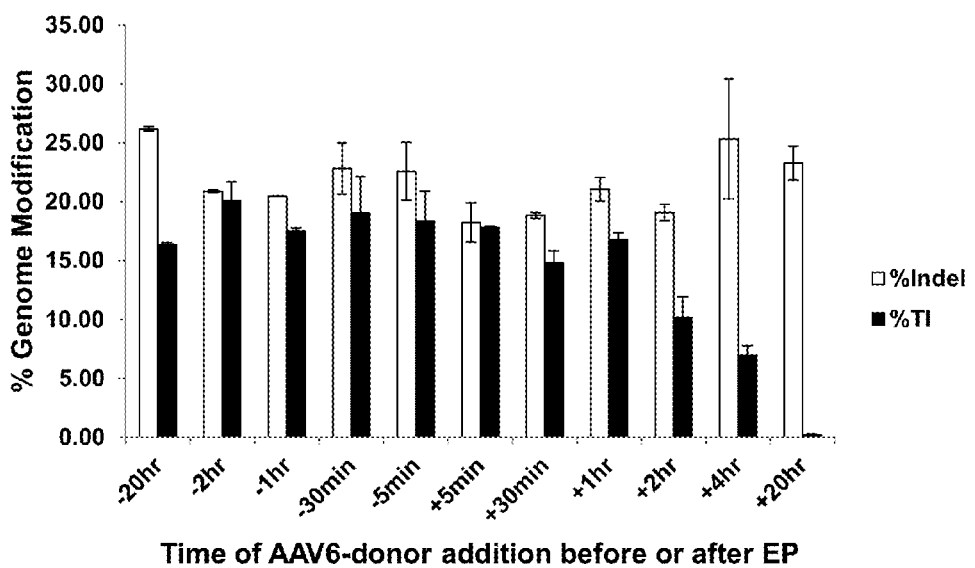

As shown in FIGS. 3A and B, short treatment (within 6 hours) with an AAV6-R5-160-XhoI donor before electroporation with the mRNA encoding the CCR5 ZFN induced more than 20% targeted integration. Slightly lower efficiency was observed at 16, 20, or 24 hour pre-treatment, whereas a significant drop in TI efficiency was observed if 48-hour pre-treatment was used. As shown in FIG. 3B, the nucleases stimulated efficient targeted integration in CD34+ cells even if donor was provided after (within 1 hour) nuclease transfection. However, a significant reduction in TI efficiency was observed when the donor was provided 4 hours after nuclease transfection, and almost no TI when the donor was provided 20 hours after nuclease transfection. The data suggested that transduction of CD34+ cells with AAV6 donor within 24 hours before or one hour after electroporation with ZFN mRNA is optimal for efficient genome modification by HDR.

Example 5

Integration of Larger Transgenes

To test whether AAV6-mediated delivery of donor is also effective for targeted integration of a larger fragment of heterologous DNA, such as a full transgene-expression cassette, a R5-pgk-GFP-pA donor, in which a pgk promoter-driven eGFP expression cassette (1.6 kb) was inserted between the CCR5 homologous arms was constructed (FIG. 4A).

CD34+ cells were treated with AAV6-R5-pgk-GFP-pA donor and CCR5 ZFN mRNA as described above, and then collected for flow cytometry analysis.

As shown in FIG. 4B, approximately 15% GFP+ cells were present in samples treated with both donor (1000 and 3000 vg/ml) and ZFN but not donor alone at 15 dpi (FIG. 4B) or at earlier time points.

The presence of targeted integration of the GFP cassette into the CCR5 locus was further confirmed using a semi-quantitative In-Out PCR assay. A set of standard controls was prepared by serial dilution of a gDNA pool of known frequency of GFP transgene integration at the CCR5 locus (determined by Southern blot) with unmodified wild-type gDNA. PCR was performed using equal amount of gDNA and a primer present in the polyA region (present in the eGFP cassette) and a primer located outside of the CCR5 homologous arm region at the 3' side of the ZFN target sites (FIG. 4C). The primers used are shown below:
5'-GAGGATTGGGAAGACAATAGCAG-3' (SEQ ID NO:9) and 5'-CCAGCAATAGATGATCCAACTCAAAT-TCC-3' (SEQ ID NO:10).

In a second set of PCR reaction, one additional primer pair, of which both located at the 5' side of the target sites and one of which is outside of the CCR5 homologous region, were also included (2 primer pairs) in the same PCR reactions. The second primer pair was used as a measurement of gDNA input. This additional primer pair is shown below:
5'-GATTTGCACAGCTCATCTGGC-3' (SEQ ID NO:11) and 5'-CCATCTTGTTCCACCCTGTGC-3' (SEQ ID NO:12).

Based on the intensity of GFP-TI bands (FIG. 4C) and the relative intensity of GFP-TI bands compared to the total CCR5 bands (FIG. 3D), CD34+ HSC/PCs treated with 1000 or 3000 vg/ml AAV6 donor and CCR5 ZFN mRNA had more than 10% of targeted integration at GFP at the CCR5 locus.

Taken together, the results confirmed that using AAV6 donor is also highly efficient for targeted integration of a larger DNA fragment with this method.

Example 6

Targeted Integration into a Second Location in the Genome

To exclude the possibility that such high efficient targeted integration is CCR5 locus-specific, an AAVS1 specific-HindIII donor was constructed in which a HindIII site was introduced between the binding sites of the AAVS1-targeting ZFN pair 30035:30054, including zinc finger proteins with 6 fingers as shown in Table 1 below. The recognition helix regions of each finger shown as F1-F6 of a single row of Table 1 and target sites bound by the ZFPs shown in the first column of Table 1. See, also, U.S. Pat. No. 8,110,379. In the target sequence, nucleotides bound by the ZFN are shown in uppercase and unbound nucleotides shown in lowercase.

TABLE 1

AAVS1-specific ZFNs, designs and target sequences

| ZFN Name Target sequence | F1 | F2 | F3 | F4 | F5 | F6 |
|---|---|---|---|---|---|---|
| 30035<br>5'-ccCCACTGT<br>GGGGTGGAGG<br>Ggacagata<br>(SEQ ID NO: 25) | RSDHLSR<br>(SEQ ID NO: 13) | TSGHLSR<br>(SEQ ID NO: 14) | YNWHLQR<br>(SEQ ID NO: 15) | RSDHLTT<br>(SEQ ID NO: 16) | HNYARDC<br>(SEQ ID NO: 17) | QNSTRIG<br>(SEQ ID NO: 18) |
| 30054<br>5'-acTAGGGAC<br>AGGATtGGTGAC<br>agaaaag<br>(SEQ ID NO: 26) | DRSNLSR<br>(SEQ ID NO: 19) | LKQHLTR<br>(SEQ ID NO: 20) | TSGNLTR<br>(SEQ ID NO: 21) | RRDWRRD<br>(SEQ ID NO: 22) | QSSHLTR<br>(SEQ ID NO: 23) | RLDNRTA<br>(SEQ ID NO: 24) |

CD34+HSPCs were treated with AAV6-AAVS1-HindIII donor and AAVS1 ZFN mRNA. Cells were collected 5 days later and processed for Illumina deep sequencing as described above using AAVS1-specific primers.

Figure 5A:
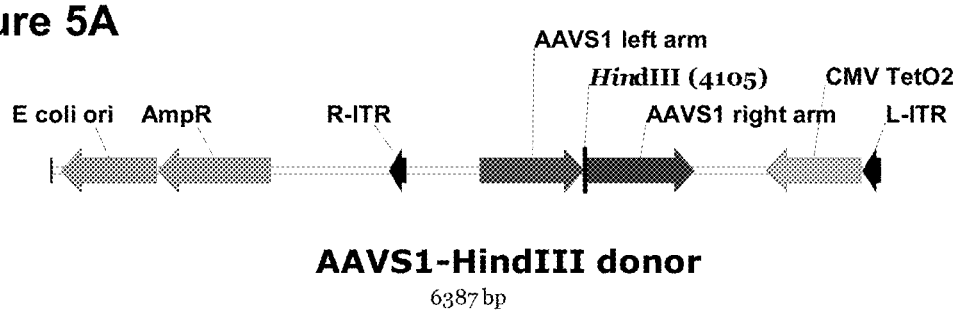
FIGS. 5A and 5B depict ZFN-AAV modification of CD34+ cells.
Figure 5B:
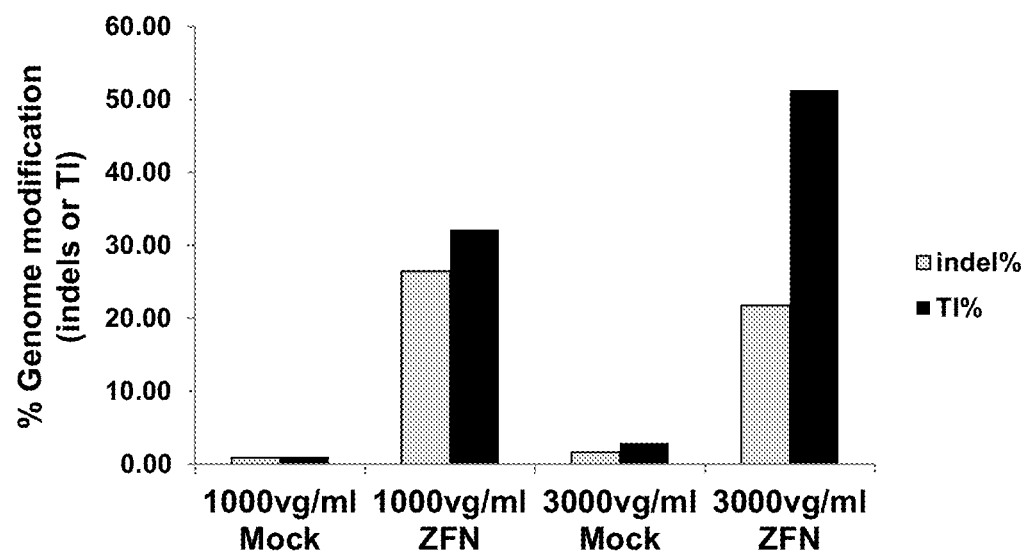

As shown in FIG. 5B, more than 30% of the alleles had targeted integration (TI) using the lower dose of AAV6 donor (1000 vg/ml), whereas more than 50% of the alleles had TI using the higher dose of AAV6 donor in the presence of AAVS1 ZFNs.

Example 7

TALEN-Mediated Targeted Integration

CD34+ cells were transduced with the AAV6-R5-160-XhoI donor (2000 vg/cell). After incubation at 37° C. for 20 hours, CCR5-specific TALEN mRNAs (80 ug/ml each) as described in U.S. Pat. No. 8,586,526 were introduced into transduced cells by electroporation using a BTX ECM830 (Harvard Apparatus). Cells were collected 5 days later for genomic DNA (gDNA) purification and processed for subsequent Illumina deep sequencing.

Figure 6:
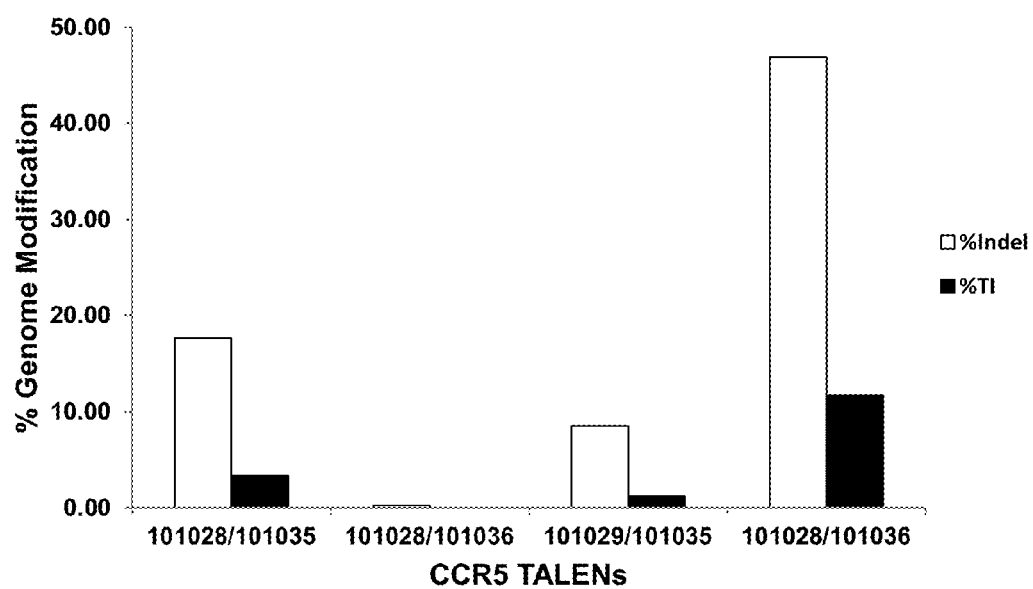
FIG. 6 is a graph depicting CCR5 modification of CD34+ cells with the indicated TALEN pairs. The graph depicts the amount of genome modification detected by Illumina deep sequencing: either insertions or deletions ("indels"), or targeted integration (TI) of the RFLP provided by the donor molecule.

FIG. 6 depicts the amount of genome modification detected by the sequencing: either insertions or deletions (indels), or targeted integration (TI) of the RFLP provided by the donor molecule. As shown, TALENs stimulated greater than 10% targeted integration of the RFLP provided by the AAV6 donor in primary CD34+ cells.

Example 8

CRISPR/Cas-Mediated Targeted Integration

CD34+ cells were transduced with the rAAV6-AAVS1-HindIII donor (500 or 2000 vg/cell). After incubation at 37° C. for 20 hours, AAVS1-specific ZFNs (30054:30035, 40 ug/ml) or Cas9 mRNA (20 ug/ml) and AAVS1-specific chimeric guide RNA (gRNA) DNA (10-40 ug/ml) were introduced into transduced cells by electroporation using a BTX ECM830 (Harvard Apparatus). The gRNA-T1 and gRNA-T2 are guide RNAs designed to bind to the following AAVS1 genomic sequences respectively: GTCCCCTC-CACCCCACAGTG$\underline{GGG}$ (SEQ ID NO:27) and GGGGC-CACTAGGGACAGGAT$\underline{TGG}$ (SEQ ID NO:28). The PAM regions are underlined. Cells were collected 5 days later for genomic DNA (gDNA) purification and processed for subsequent Illumina deep sequencing.

Figure 7A:
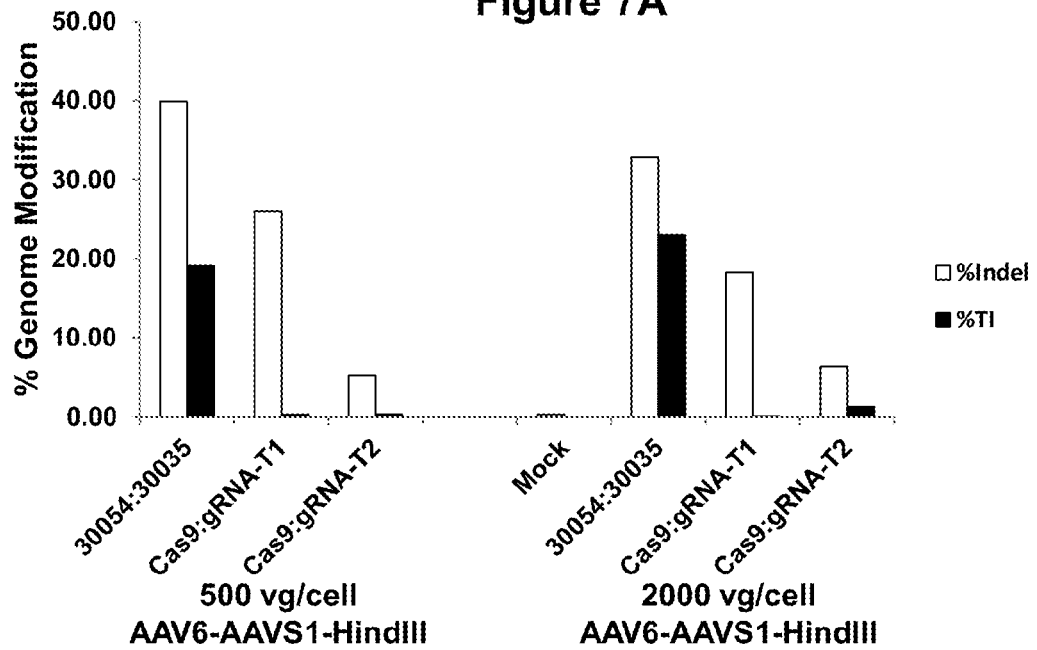
FIGS. 7A and 7B are graphs depicting CRISPR/Cas9-mediated targeted integration of a RFLP (HindIII site) provided by an AAV6 donor into the AAVS1 locus using the indicated nucleases. The same AAVS1 region (cleavage sites are less than 25 bp away) is targeted by the AAVS1 ZFN pair (30054:30035) and CRISPR/Cas9 reagents ("Cas9-gRNA-T1" and "Cas9-gRNA-T2") "T-1" and "T-2" indicate different guide RNAs.
Figure 7B:
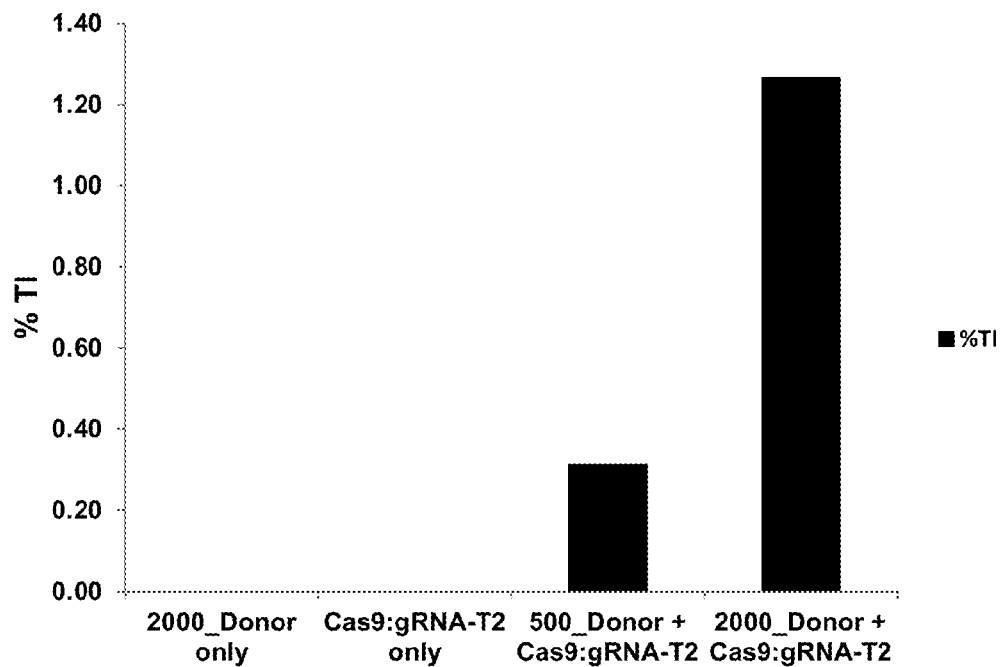

FIG. 7 depicts the amount of genome modification detected by the sequencing: either insertions or deletions (indels), or targeted integration (TI) of the RFLP provided by the donor molecule. As shown, CRISPR/Cas9 stimulated greater than 1% targeted integration of the RFLP provided by the AAV6 donor in primary CD34+ cells in this experiment.

Example 9

AAV Transduction and TI in CD4+ T Cells

Primary CD4+ T cells were transduced with the AAV2, AAV5, AAV6, AAV8 or AAV9 vectors containing a CMV-driven eGFP transgene in the presence of IL2 (20 ng/ml) and Dynabeads® Human T-Activator CD3/CD28 (Life Technology). Cells were then collected at 5 days post-infection (dpi) and analyzed using a flow cytometer (Guava, Millipore).

The frequency (%) of GFP positive cells is shown below in Table 2. AAV6 transduced primary CD4+ T cells with the highest efficiency compared to other serotypes (AAV2, AAV5, AAV8, and AAV9).

TABLE 2

| AAV serotype-dependent GFP reporter transduction in CD4+ T cells | | | | | |
|---|---|---|---|---|---|
| Dose (vg/cell) | AAV2 | AAV5 | AAV6 | AAV8 | AAV9 |
| 3000 | 1.00 | 0.36 | 0.05 | 0.11 | 0.11 |
| 1.00E+04 | 3.30 | 1.88 | 0.46 | 0.21 | 0.26 |
| 3.00E+04 | 7.64 | 4.41 | 3.59 | 0.57 | 0.69 |
| 1.00E+05 | 19.19 | 13.27 | 30.52 | 2.10 | 2.49 |
| 3.00E+05 | 31.86 | 25.67 | 88.34 | 5.98 | 5.58 |

In addition, CD4+ cells were transduced with the indicated doses of rAAV2, rAAV6, or IDLV R5-160-XhoI donor. After incubation at 37° C. for 20 hours, CCR5- or AAVS1-specific ZFN mRNAs (60 ug/ml) were introduced into transduced cells by electroporation using a BTX ECM830 (Harvard Apparatus). Cells were collected 4 days later for genomic DNA (gDNA) purification and processed for subsequent Illumina deep sequencing.

FIG. 8 depicts the amount of genome modification detected by the sequencing: either insertions or deletions (indels), or targeted integration (TI) of the RFLP provided by the donor molecule in CCR5-nuclease (FIG. 8A) and AAVS1-nuclease (FIG. 8B) treated CD4+ T cells. As shown, ZFNs stimulated more than 40% targeted integration of the RFLP provided by the AAV6 donor in primary CD4+ cells.

Example 10

AAV Transduction and TI in CD8+ T Cells

Primary CD8+ T cells were transduced with the AAV2, AAV5, AAV6, AAV8 or AAV9 vectors containing a CMV-driven eGFP transgene in the presence of IL2 (20 ng/ml) and Dynabeads® Human T-Activator CD3/CD28 (Life Technology). Cells were then collected at 5 days post-infection (dpi) and analyzed using a flow cytometer (Guava, Millipore).

The frequency (%) of GFP positive cells is shown below in Table 3. AAV6 transduced CD8+ T cells with the highest efficiency at relatively lower doses compared to other serotypes (AAV2, AAV5, AAV8, and AAV9).

TABLE 3

| AAV serotype-dependent GFP reporter transduction in CD8+ T cells | | | | | |
|---|---|---|---|---|---|
| Dose (vg/cell) | AAV2 | AAV5 | AAV6 | AAV8 | AAV9 |
| 1.00E+04 | 1.06 | 0.71 | 1.20 | 0.22 | 0.33 |
| 3.00E+04 | 2.62 | 2.04 | 7.30 | 0.79 | 0.60 |
| 1.00E+05 | 7.97 | 4.87 | 25.06 | 1.19 | 1.70 |
| 3.00E+05 | 12.08 | 10.74 | 68.25 | 4.65 | 3.70 |
| 1.00E+06 | 21.74 | 19.66 | 78.06 | 12.32 | 10.65 |
| 3.00E+06 | 28.44 | 31.95 |  | 24.80 | 18.36 |

In addition, CD8+ cells were transduced with the indicated doses of rAAV2, rAAV6, or IDLV R5-160-XhoI donor. After incubation at 37° C. for 20 hours, CCR5- or AAVS1-specific ZFN mRNAs were introduced into transduced cells by electroporation using a BTX ECM830 (Harvard Apparatus). Cells were collected 4 days later for genomic DNA (gDNA) purification and processed for subsequent Illumina deep sequencing. FIG. 9 depicts the amount of genome modification detected by the sequencing: either insertions or deletions (indels), or targeted integration (TI) of the RFLP provided by the donor molecule in CCR5-nuclease (FIG. 9A) and AAVS1-nuclease (FIG. 9B) treated CD8+ T cells. As shown, ZFNs stimulated more than 30% targeted integration of the RFLP provided by the AAV6 donor in primary CD8+ cells.

Example 11

Ex Vivo Methods

The genetically modified cells, including CD34+ HSPCs (e.g., patient-derived CD34+ cells and/or modified CD4+ and/or CD8+ T cells) as previously described (Aiuti et al. (2013) *Science* 341, 1233151), expressing IL2RG as described herein are administered to subjects as previously described (Aiuti et al. ibid), resulting in long-term multilineage engraftment in subjects treated with the modified cells.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of integrating one or more transgenes into a genome of an isolated population of hematopoietic stem cells or T-cells, the method comprising:
introducing, into the population of hematopoietic stem cells or T-cells, (a) an adeno-associated type 6 (AAV6) donor vector comprising the one or more transgenes and (b) at least one non-naturally occurring nuclease, wherein the at least one nuclease is introduced in mRNA form and cleaves the genome of the population of hematopoietic stem cells or T-cells such that the one or more transgenes are integrated into the genome of the cell, wherein the donor vector is introduced into the cell prior to or after the at least one nuclease and further wherein
(i) if the donor vector is introduced into the population of hematopoietic stem cells or T-cells before the at least one nuclease, the at least one nuclease is introduced into the cell 3 to 48 hours after the donor vector is introduced and;
(ii) if the at least one nuclease is introduced before the donor vector, the donor vector is introduced into the cell within 4 hours after the at least one nuclease is introduced,
such that at least 10% of the one or more transgenes are integrated into the genome of the population of hematopoietic stem cells or T-cells.

2. The method of claim 1, wherein the donor vector is introduced into the cell before the at least one nuclease and the cell is cultured for between 1 and 24 hours after the donor vector is introduced into the cell.

3. The method of claim 1, wherein the AAV6 vector comprises an AAV6 chimeric vector.

4. The method of claim 1, wherein the at least one nuclease is selected from the group consisting of a zinc finger nuclease (ZFN), a TALE nuclease (TALEN), a CRISPR/Cas nuclease system and combinations thereof.

5. The method of claim 1, wherein the nuclease cleaves a safe-harbor gene.

6. The method of claim 5, wherein the safe-harbor gene is selected from the group consisting of a CCR5 gene, an AAVS1 gene, a Rosa gene and an albumin gene.

7. The method of claim 1, wherein the transgene encodes a therapeutic protein.

* * * * *